(12) United States Patent
Webb

(10) Patent No.: US 10,287,020 B2
(45) Date of Patent: May 14, 2019

(54) ARM SUPPORT APPARATUS

(71) Applicant: Daniel Scott Webb, Greenwood Village, CO (US)

(72) Inventor: Daniel Scott Webb, Greenwood Village, CO (US)

(*) Notice: Subject to any disclaimer, the term of this patent is extended or adjusted under 35 U.S.C. 154(b) by 417 days.

(21) Appl. No.: 15/291,012

(22) Filed: Oct. 11, 2016

(65) Prior Publication Data

US 2017/0036573 A1 Feb. 9, 2017

Related U.S. Application Data

(63) Continuation-in-part of application No. 14/177,040, filed on Feb. 10, 2014, now abandoned.

(60) Provisional application No. 61/762,943, filed on Feb. 10, 2013.

(51) Int. Cl.
| | |
|---|---|
| *A41D 13/00* | (2006.01) |
| *B64D 11/06* | (2006.01) |
| *A61F 5/37* | (2006.01) |
| *A47C 7/54* | (2006.01) |
| *A47C 16/00* | (2006.01) |
| *A47G 9/10* | (2006.01) |
| *B60N 2/75* | (2018.01) |

(52) U.S. Cl.
CPC .......... *B64D 11/0646* (2014.12); *A47C 7/543* (2013.01); *A47C 16/00* (2013.01); *A47G 9/1063* (2013.01); *A61F 5/3715* (2013.01); *A61F 5/3746* (2013.01); *B60N 2/75* (2018.02)

(58) Field of Classification Search
CPC ....... A61F 5/3746; A41D 27/08; A41D 15/04; A41D 13/04; A41D 13/0575; A41D 3/08
USPC .................................................... 2/69; 602/4
See application file for complete search history.

(56) References Cited

U.S. PATENT DOCUMENTS 2,560,243 A * 7/1951 Peterson ............... A61F 5/3746
602/4

* cited by examiner

*Primary Examiner* — Timothy K Trieu
(74) *Attorney, Agent, or Firm* — Roger A. Jackson

(57) ABSTRACT

A human arm support apparatus for use with a human seated, the apparatus includes a flexible planar member having a front end portion and a rear end portion; an aperture larger than a human head is therethrough the planar member with the aperture passed over the human head for the planar member to rest against a human's shoulders. Further included is a flexible surrounding sidewall affixed to the front end portion for receiving a human's arms to be supported, wherein the support comes from the rear end portion being wedged between the buttocks of the human and the seat, thus the aperture does not contact or put pressure upon the neck of the human.

6 Claims, 15 Drawing Sheets

ARM SUPPORT APPARATUS

RELATED PATENT APPLICATION

This is a continuation in part (CIP) patent application of U.S. patent application Ser. No. 14/177,040 filed on Feb. 10, 2014 by Daniel Scott Webb of Greenwood Village, Colo., U.S., that claims benefit of U.S. provisional patent application Ser. No. 61/762,943 filed on Feb. 10, 2013 by Daniel Scott Webb of Greenwood Village, Colo., U.S.

TECHNICAL FIELD

The present invention relates generally to an apparatus for retaining a user's arms for support and comfort. More specifically, the present invention relates to the field of a portable and removably engagable clothing accessory for increasing the user's comfort during extended time periods on sitting in side by side seating in common carriers such as airlines, trains, buses, and the like.

BACKGROUND OF INVENTION

Worldwide, common carrier travel either through plane, train, bus, and similar conveyances is utilized by millions of individuals daily who typically sit in row seating that is minimal in size wherein two side by side seats typically share an armrest that is usually narrow in size. Thus the typical armrest can usually barely accommodate a single user's arm, and certainly not two adjacent passengers' arms comfortably. For shorter duration trips, i.e. commutes up to an hour, this armrest sharing issue is usually a minor inconvenience for most individuals on the common carrier. However, for longer trips, for instance greater than one hour, this armrest sharing issue can easily go from a minor inconvenience to a major inconvenience due to increased sitting fatigue, restlessness, inadvertent shifting movement of the user's arms thus accidently bumping into their neighbor passenger's arms or torso, causing an uncomfortable situation, as neighboring passengers simply want to pass the hours of time in their seat as easily and comfortably as possible. Of course this inadvertent bumping of the adjacent passenger, would most likely wake them up if they were dozing further causing an annoying situation.

In addition, to the previously described undesirable passenger bumping situation, having a way to comfortably secure and store a user's arms for themselves would increase the user's ability to comfortably doze off themselves helping to pass the hours in the cramped and tight seat quarters that they are in, thus reducing arm and shoulder fatigue for the duration of the trip. There has been recognition of this issue, mainly how to make a row seat somewhat comfortable for a significant amount of time on having to be seated for up to eighteen hours or more on an oversees airline flight. Solutions to making a confined row seat comfortable include inflatable back lumbar supports, padded neck collars, and a front inflatable pillow for a passenger to place their face upon. While these solutions have their merits, there is a major consideration of the higher volume and weight that these solutions have, as these are to be carried by the traveler passenger, where space and weight considerations are at a premium.

With the ever increasing limitations upon carry-on bags for weight and size by the common carriers, any additional bulk and weight that these seat comfort solutions provide must be minimal. Further, a consideration of the convenience of setting up the seat comfort device needs to be considered, i.e. if it needs manual inflating/deflating to stow and take with you-this is an inconvenience to consider, plus is the seating comfort solution bulky and or heavy-if so, this could be a major drawback, because travelling "light" these days is more important than ever, especially with the previously mentioned carrier restrictions on carry-on items. In addition, for the seat comfort device, if a number of straps/buckles are required, this further adds to the inconvenience, as the seat comfort device must be deployed and taken down for each leg of the traveler's trip, making for multiple setups and takedowns, adding extra time and hassle. Also, another consideration is safety, as when the traveler is using the seat comfort device, in case of an emergency, i.e. wherein the traveler would have to quickly exit their seat, the seat comfort device cannot impede the traveler's exit from the seat in any manner, as the traveler must be able to leave their seat and the seat comfort device without having to take apart of disengage anything related to the seat comfort device. Thus it is imperative that that passenger seating comfort device be of absolutely minimal size and weight to be a minimal inconvenience to the user to take with them on their travels.

The following prior art examines some of the existing solutions to passenger seat fatigue solutions. Starting with U.S. Pat. No. 6,966,069 to Booth disclosed is a travel blanket having a round elastically bordered head hole through which a traveler can extend around the traveler's head, resulting in a travel blanket that doesn't slip off downward off of the traveler's shoulders and chest. In Booth, a shortened rear portion of the blanket drapes down over a portion of the traveler's back and shoulders via just covering the shoulder blades, basically for warmth of the top of the shoulders only without a need for covering the traveler's back, as the seat back provides warmth, see FIG. 1.

Further, in Booth a much longer front portion covers the traveler's chest, torso, arms, and legs/feet resulting in somewhat of a backless blanket type poncho. Also in Booth, a pocket is positioned along the interior of the front portion for supporting the traveler's arms when the traveler's arms are positioned therein, an option for multiple pockets at different positions is also offered, such that the traveler's arms may both be placed into one pocket or the traveler's arms may be placed into their own separate pockets. Wherein in Booth, the downward weight force of the traveler's arms is retained primarily by the rounded elastic neck opening resting as against the traveler's neck and somewhat by the shortened rear portion, however, if the traveler leans forward in the airplane seat a small amount, the round neck opening will bear the arm weight pull down force as against the traveler's neck solely, making for an uncomfortable situation with the fabric edge pulling against the traveler's neck.

Next, in U.S. Pat. No. 2,560,243 to Peterson, disclosed is a shoulder rest double arm sling comprising a T-shaped sheet of flexible material, the laterally extending arms of the T-shaped sheet being adapted to embrace or encompass the waist of the wearer similar to a backpack, with fastening means on the outer end portions of the arms for securing the arms together. Further in Peterson, the stem portion of the T-shaped sheet is slotted plus centrally and vertically terminating in an elongated oval-shaped opening below the plane of the arms, in which an opening is adapted to accommodate the neck of the wearer, the material of the stem portion at opposite sides of the slotted opening comprising a pair of furcations, which are substantially parallel and are spaced from each other. Also in Peterson, the upper portions of the furcations being adapted to rest on the shoulders of the wearer, and the lower portions of each of the furcations terminating in a sling, with the sling being adjustable whereby the elevation and position of each sling relative to the oval-shaped opening may be changed.

Peterson essentially transfers the arm weight downward force loading from the shoulders only-as is with a typical arm sling, to the wearer's waist-being somewhat like a hiker's or camper's backpack that transfers the bulk of the backpack weight from the wearer's shoulders to their waist or hips, which results on greater comfort, as the wearer's waist or hips can accommodate the weight or force with less long term fatigue than a wearer's shoulders for the same amount of force of weight over extended periods of time.

Continuing, in U.S. Pat. No. 8,197,429 to Neseem, disclosed is a double arm sling, including two pouches, each of the two pouches configured for individually receiving one of a patient's arms, and at least one pair of half-straps. In Neseem, the pair of half-straps is configured to fasten the double arm sling around the torso of the patient. The double arm sling in Neseem may further include at least one pair of tongues coupled to the two pouches and coupled to at least one pair of half-straps, a backing portion coupled to the two pouches, and at least one back pad configured to receive the at least one pair of half straps. Neseem, like Peterson attempts to take the arm weight load or force from the wearer's shoulders, however, Neseem putting the load at mid-torso with multiple padded straps fastened about the wearer's midsection torso.

Further, in U.S. Pat. No. 6,453,904 to Wilson, et al. disclosed is an arm-sling vest that includes sleeveless front and back vest panels defining an opening permitting the panels to fit over a person's head so as to rest upon the shoulders. In Wilson et al., lateral edges of the panels include hook and loop fasteners for releasably and adjustably connecting the panels together about a person's torso. Further, in Wilson et al., a pair of support straps are attached to an outer surface of the front vest panel and include free ends extending therefrom. A corresponding pair of retainer patches in Wilson et al., are attached to the front vest panel and positioned above the support straps and aligned therewith, respectively.

The support straps and retainer patches in Wilson et al., include complementary fasteners such that the straps may cradle a person's forearm and be secured to a respective retainer patch. The support straps in Wilson et al., are independently operable such that a person's forearm may be cradled in a plurality of orientations. Wilson et al., somewhat like Peterson and Neseem, transfers a portion of the arm load weight and force away from just the shoulders to more of the entire torso through a snug fitting vest, via attempting to create a larger load bearing surface area as against the torso, thus relieving the shoulders from bearing the entire arm weight force loading, although in transferring the arm weight force to the torso, care must be given to not wrapping the vest about the torso so firmly as to cause discomfort from the torso being overly compressed to interfere with torso movement of human breathing.

Continuing, in the prior art in U.S. Pat. No. 5,141,488 to Schrader disclosed is a sling device for securing to a waistband of a user. The sling device in Schrader extends over the left and right shoulders of the user for supporting an arm of the user. In Schrader, the device includes a first and second strap extending over the left and right shoulder of the user respectively. Each of the straps in Schrader has a first and a second end. Front and further front fasteners in Schrader are connected to the first end of the first and second straps respectively for fastening the first ends of the straps to the user's waistband. Rear and further fasteners are also connected in Schrader to the second ends of the first and second straps respectively for fastening the second ends to the waistband.

Further, in Schrader a first and second portion each having a first and second extremity are secured at the first extremities to the first and second straps respectively between the front and further front fasteners and the left and right shoulders respectively of the user. Also, in Schrader adjustable and further adjustable securing elements are secured to the second extremities of the first and second portions respectively for adjustably securing the second extremities to the first and second portions respectively between the first and second extremities thereof such that the first and second portions define an adjustable loop and a further adjustable loop respectively for adjustably supporting the arm of the user. Schrader being also somewhat like, Wilson et al., Peterson, and Neseem, removes a portion of the arm weight force from the user's shoulders via attachment to the waistband of the user, however, Schrader's narrow straps would still load the user's shoulders from the arm weight force to some extent, appearing to be close in design to pants suspenders in sizing and configuration.

What is needed is a portable, mobile, and easily removably engagable arm support apparatus that doesn't require straps, clasps, fasteners, hooks or any other type of hardware for supporting the user's arm weight or force, while the user's arm(s) are disposed within a sling, thus greatly simplifying putting on and taking off of the arm support apparatus, also resulting in a much smaller, lighter, and easy to carry apparatus. Further as previously identified in the cited prior art, reducing the arm weight force loading on the user's shoulders would be greatly desired in addition to having no loading as against the user's neck, however, in considering where that arm weight load is transferred to so as to not cause discomfort in another part of the user's body via adding loading where there was no loading before.

SUMMARY OF INVENTION

Broadly, the present invention of the human arm support apparatus is for use with a human seated only upon an ottoman, meaning not having a seat back or seat arms, with the human having a head, neck, shoulders, back, chest, arms, and buttocks for reference. The human arm support apparatus includes the flexible planar member having the exterior surface and the opposing interior surface. The flexible planar member also having the front end portion and the opposing rear end portion with the longitudinal axis spanning therebetween. The flexible planar member also having the first side portion and the opposing second side portion with the transverse axis spanning therebetween, further, a slot shaped aperture is positioned therethrough the flexible planar member from the exterior surface to the interior surface, the slot has a longer major axis coincident with the longitudinal axis and the slot has a shorter minor axis coincident with the transverse axis. Also, the aperture is sized and configured to be larger than the human head to freely pass over the human head to rest against the human's shoulders, such that the aperture is not in contact with a human neck. In addition, the transverse axis is positioned to be asymmetrically closer to the front end portion and the transverse axis is positioned to be asymmetrically further from the rear end portion.

Further included in the human arm support apparatus is the flexible surrounding sidewall that is about the lengthwise axis, with the sidewall having an inside surface that defines a sidewall interior and the sidewall also having the outside surface, wherein a portion of the outside surface is affixed to the exterior surface on the front end portion being positioned such that the lengthwise axis is parallel to the transverse axis. Operationally and in use the aperture is freely passed over the human head with the interior surface resting against the human shoulders, with the sidewall being positioned adjacent to the human chest and the rear end portion is draped over the human back and continuing beyond the human buttocks, the human then sits upon the ottoman essentially sitting on a part of the rear end portion thus the part is disposed as between the ottoman and the human buttocks. Further, the front end portion interior surface is adjacent to the human chest, wherein the human arms are then positioned adjacent to the exterior surface of the front end portion wherein a portion of the human arms are manually disposed within the interior to act as a hanging support for the arms, wherein the arms weight results in a downward force on the front end portion that translates to an upward force on the rear end portion that is completely supported by the frictional interference as between the rear end portion that is disposed between the human buttocks and the ottoman resulting in no contact of the aperture upon the human neck from the downward force to maximize comfort for the human.

These and other objects of the present invention will become more readily appreciated and understood from a consideration of the following detailed description of the exemplary embodiments of the present invention when taken together with the accompanying drawings, in which;

REFERENCE NUMBERS IN DRAWINGS

Figure 1:
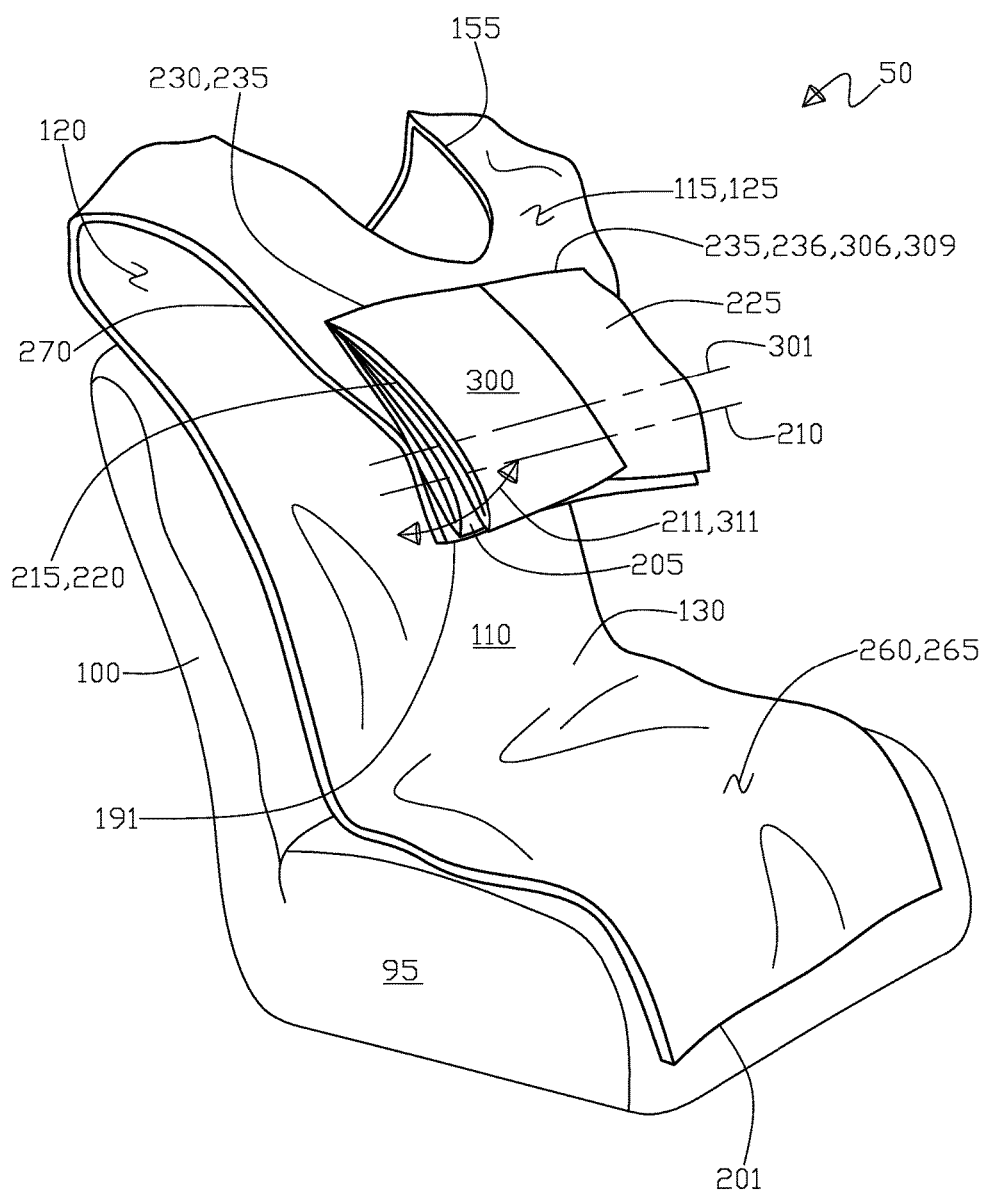
FIG. 1 shows a perspective view of the arm support apparatus in its typical use configuration in relation to the seat, except with the human removed for pictorial clarity, thus is shown the seat back, the flexible planar member, the exterior surface, the interior surface, the front end portion, the rear end portion, the first side portion, the second side portion, the slot shaped aperture, the surrounding sidewall, the inside surface of the sidewall, interior of the sidewall, outside surface of the sidewall, portion of the outside surface, affixing of the portion, and where the rear end portion is disposed on the seat and human buttocks (not shown)

50 Arm support apparatus
55 Human
60 Head of human 55
65 Neck of human 55
70 Shoulders of human 55
75 Back of human 55
80 Chest of human 55
85 Arms of human 55
86 Hands of human 55
87 Elbow of the human 55
90 Buttocks of human 55
95 Ottoman type chair or seat
100 Back of chair or seat 95
105 Arms of chair or seat 95
110 Flexible planar member
115 Exterior surface of flexible planar member 110
120 Interior surface of flexible planar member 110
125 Front end portion of flexible planar member 110
126 First side margin of flexible planar member 110
130 Rear end portion of flexible planar member 110
131 Second side margin of flexible planar member 110
132 Side distance between the first side margin 126 and the second side margin 131
135 Longitudinal axis of flexible planar member 110
140 First side portion of flexible planar member 110
145 Second side portion of flexible planar member 110
150 Transverse axis of flexible planar member 110
155 Slot shaped aperture of flexible planar member 110
156 Aperture width parallel to the transverse 150 and minor 165 axes
157 Aperture length parallel to the longitudinal 135 and major 160 axes
160 Major axis of slot shaped aperture 155
165 Minor axis of slot shaped aperture 155
170 Coincident relationship of major axis 160 and longitudinal axis 135
175 Coincident relationship of minor axis 165 and transverse axis 150
180 Freely passing of the aperture 155 over the human head 60
185 Resting as against the shoulders 70 of the aperture 155
190 Transverse axis 150 being asymmetrically closer to the front end portion 125 defined as a front portion distance as between the front margin 191 and the aperture 155 transverse axis 150
191 Front margin of the front end portion 125
200 Transverse axis 150 being asymmetrically further from the rear end portion 130 defined as a rear portion distance as between the rear margin 201 and the aperture 155 transverse axis 150
201 Rear margin of the rear end portion 130
205 Flexible surrounding sidewall
206 Flexible outbound surrounding sidewall extended to encompass the elbow 87
210 Lengthwise axis of the flexible surrounding sidewall 205
211 Pivotal movement of the lengthwise axis 210 and the surrounding sidewall 205
215 Inside surface of the flexible surrounding sidewall 205
220 Interior of the flexible surrounding sidewall 205
225 Outside surface of the flexible surrounding sidewall 205
230 Portion of the outside surface 225
235 Affixing of the portion 230 of the outside surface 225 the exterior surface 115
236 Single straight transverse line attachment of the affixing 235 of the portion 230 of the outside surface 225 the exterior surface 115
240 Positioning of the lengthwise axis 210 being parallel to the transverse axis 150
245 Sidewall positioned adjacent to the human chest 80
250 Rear end portion 130 being draped over the human back 75 and continuing past the human buttocks 90
255 Human 55 sitting on the ottoman 95 and sitting upon the rear end portion 130
260 Part of the rear end portion 130 disposed as between the ottoman 95 and the human buttocks 90
265 Frictional interference of the rear end portion 130 disposed 260 as between the ottoman 95 and the human buttocks 90
270 Interior surface 120 of the front end portion 125 being adjacent to the human chest 80
275 Positioning the human arms 85 being adjacent to the exterior surface 115 of the front end portion 125
280 Portion of the human arms 85 manually disposed within the interior 220 of the sidewall 205
285 Weight of the arms 85 creating a downward force or from the arms 85 pushing away from the chest 80
290 Upward force translated from downward force 285
291 Inward force from the outbound surrounding sidewall 206
295 No contact of aperture 155 upon the human neck 65 from the downward force 285 or from the arms 85 pushing away from the chest 80
300 First alternate branched configuration of the surrounding sidewall 205 for hand 86 access for pivotal movement 311 and rotational movement 313 of the hand 86 to accommodate eating, drinking, working on laptop computers, working on tablet computers, playing game consoles, and the like 301 Branched sidewall 300 axis 302 Inside surface of the branched sidewall 300

303 Outside surface of the branched sidewall 300

304 Portion of the outside surface 303

305 Face pillow in a "U" shape with an open center-similar to a massage table face pillow or face support 306 Affixing of the portion 304 of the outside surface 303 the exterior surface 115

307 Positioning of the lengthwise axis 301 being parallel to the transverse axis 150

308 Branched sidewall 300 positioned adjacent to the human chest 80

309 Split single transverse line attachment of the affixing 306 of the portion 304, 440 of the outside surface 303, 430 the exterior surface 115

310 Desk or tray table

311 Pivotal movement of the branched sidewall axis 301, 410 and the branched surrounding sidewall 300

312 Interior of the branched sidewall 300

313 Rotational movement from the branched sidewall 300 and the split attachment 309

400 Second alternate branched outbound configuration of the surrounding outbound sidewall 206 for hand 86 access for pivotal movement 311 and rotational movement 313 of the hand 86, and to encompass the elbows 87 causing inward force 291 to accommodate eating, drinking, working on laptop computers, working on tablet computers, playing game consoles, and the like to keep the elbows 87 from moving outward toward an adjoining chair (not shown) or spilling outward over the chair 95 arm 105

410 Lengthwise axis for the outbound surrounding sidewall 206

420 Inside surface of the outbound surrounding sidewall 206

430 Outside surface of the outbound surrounding sidewall 206

440 Portion of the outside surface 430 of the outbound surrounding sidewall 206

450 Interior of the surrounding outbound sidewall 206

460 Inner edge margin of the surrounding outbound sidewall 206

470 Outer edge margin of the surrounding outbound sidewall 206

480 Extension distance of the outer edge margin 470 beyond the first side margin 126 and second side margin 131

DETAILED DESCRIPTION

Figure 2:
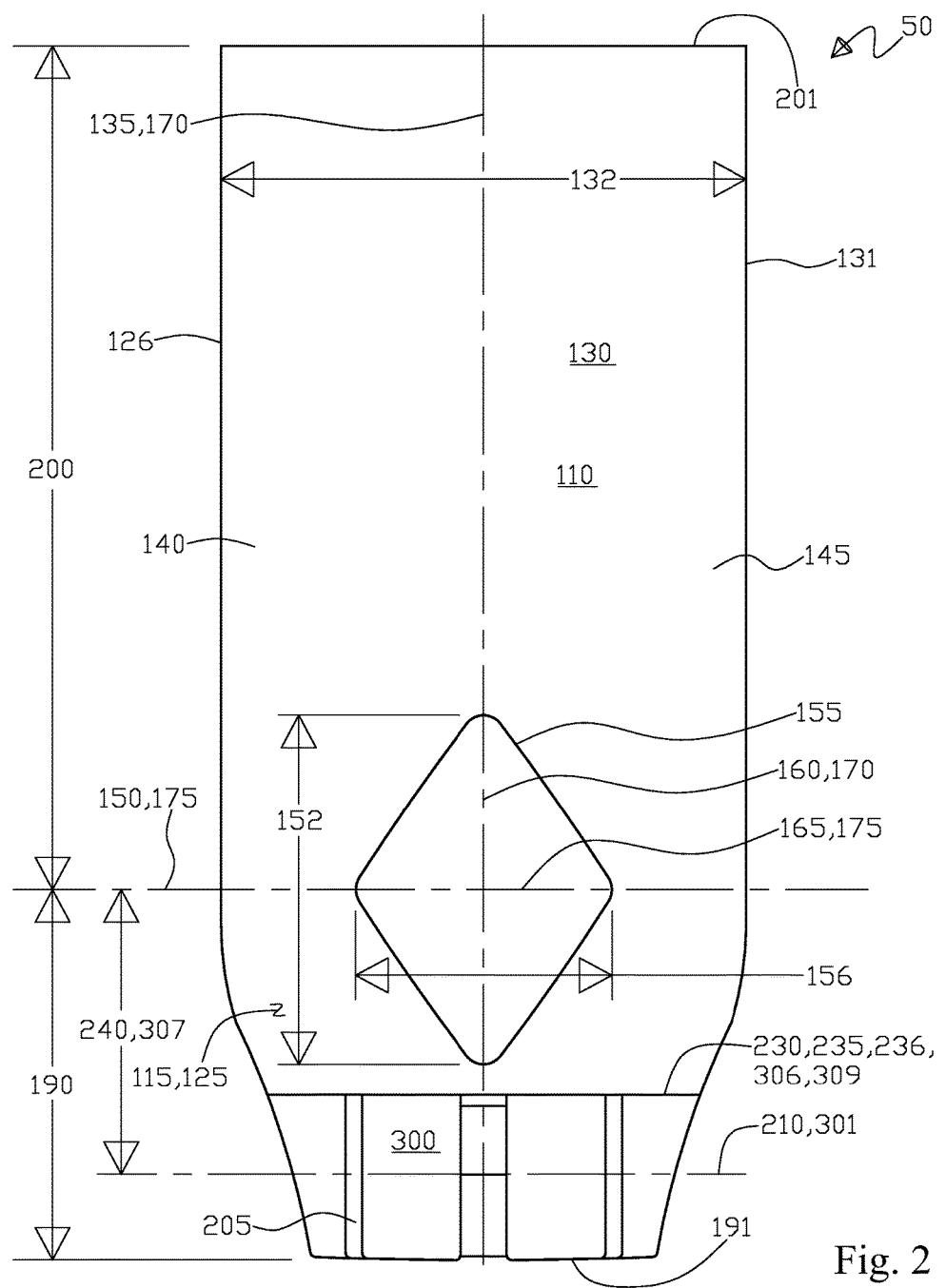
FIG. 2 shows a flat pattern view of the arm support apparatus from the exterior surface side of the flexible planar member, thus also shown is the front end portion, the rear end portion, the longitudinal axis, the first side portion, the second side portion, the transverse axis, the slot shaped aperture, the major axis, the minor axis, the coincident relationship of the major axis and longitudinal axis, the coincident relationship of the minor axis and transverse axis, the transverse axis being asymmetrically closer to the front end portion, the transverse axis being asymmetrically further from the rear end portion, the surrounding sidewall, the lengthwise axis, outside surface of the sidewall, portion of the outside surface, affixing of the portion, and positioning of the lengthwise axis being parallel to the transverse axis.

With initial reference to FIG. 1 shown is the perspective view of the arm support apparatus 50 in its typical use configuration in relation to the seat 95, except with the human 55 removed for pictorial clarity, thus is shown the seat back 100, the flexible planar member 110, the exterior surface 115, the interior surface 120, the front end portion 125, the rear end portion 130, the first side portion 140, the second side portion 145, and the slot shaped aperture 155. Further shown in FIG. 1 is the surrounding sidewall 205, the inside surface 215 of the sidewall 205, the interior 220 of the sidewall 205, the outside surface 225 of the sidewall, the portion 230 of the outside surface 225, affixing 235 of the portion 230, and where the rear end portion 130 is disposed on the seat 95 and human buttocks 90 (not shown);

Next, FIG. 2 shows a flat pattern view of the arm support apparatus 50 from the exterior surface 115 side of the flexible planar member 110, thus also shown is the front end portion 125, the rear end portion 130, the longitudinal axis 135, the first side portion 140, the second side portion 145, the transverse axis 150, the slot shaped aperture 155, the major axis 160, the minor axis 165, the coincident relationship 170 of the major axis 160 and longitudinal axis 135, the coincident relationship 175 of the minor axis 165 and the transverse axis 150. Also, FIG. 2 shows the transverse axis 150 being asymmetrically closer 190 to the front end portion 125, the transverse axis 150 being asymmetrically further 200 from the rear end portion 130, the surrounding sidewall 205, the lengthwise axis 210, outside surface 225 of the sidewall 205, the portion 230 of the outside surface 225, affixing 235 of the portion 230, and positioning 240 of the lengthwise axis 210 being parallel to the transverse axis 150.

Figure 3:
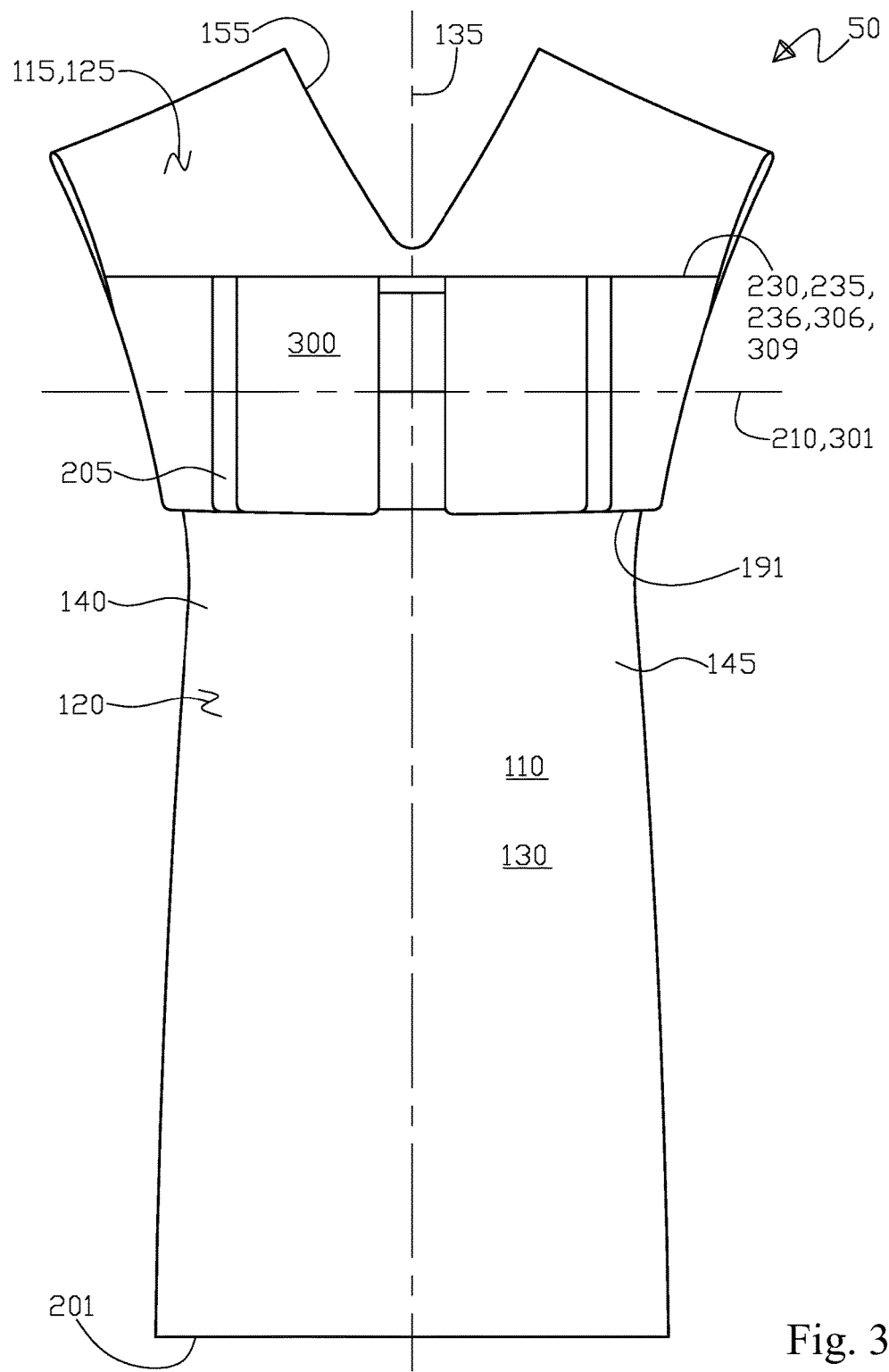
FIG. 3 shows a folded pattern view of the arm support apparatus from the exterior surface side for the front end portion and the interior surface of the rear end portion all of the flexible planar member, the longitudinal axis, the first side portion, the second side portion, the slot shaped aperture, the surrounding sidewall, the lengthwise axis, outside surface of the sidewall, portion of the outside surface, and affixing of the portion.
Figure 4:
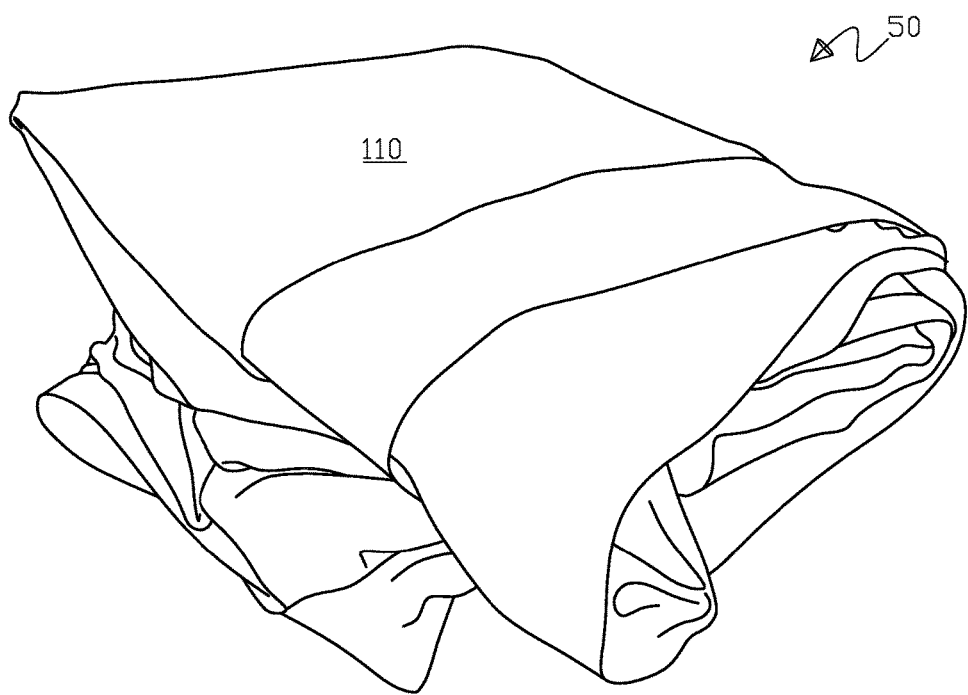
FIG. 4 shows a perspective view of the arm support apparatus in a folded up state for stowing or transporting.

Continuing, FIG. 3 shows a folded pattern view of the arm support apparatus 50 from the exterior surface side 115 for the front end portion 125 and the interior surface 120 of the rear end portion 130 all being of the flexible planar member 110, the longitudinal axis 135, the first side portion 140, the second side portion 145, the slot shaped aperture 155, the surrounding sidewall 205, the lengthwise axis 210, outside surface of the sidewall 225, portion 230 of the outside surface 225, and affixing 235 of the portion 230. Next, FIG. 4 shows a perspective view of the arm support apparatus 50 in a folded up state for stowing or transporting, which is a small package being about one-quarter inch thick by twelve inches long by nine inches wide, weighing about one-half pound-being helped by the fact there are no belts, straps, buckles, or fasteners to accommodate.

Figure 5:
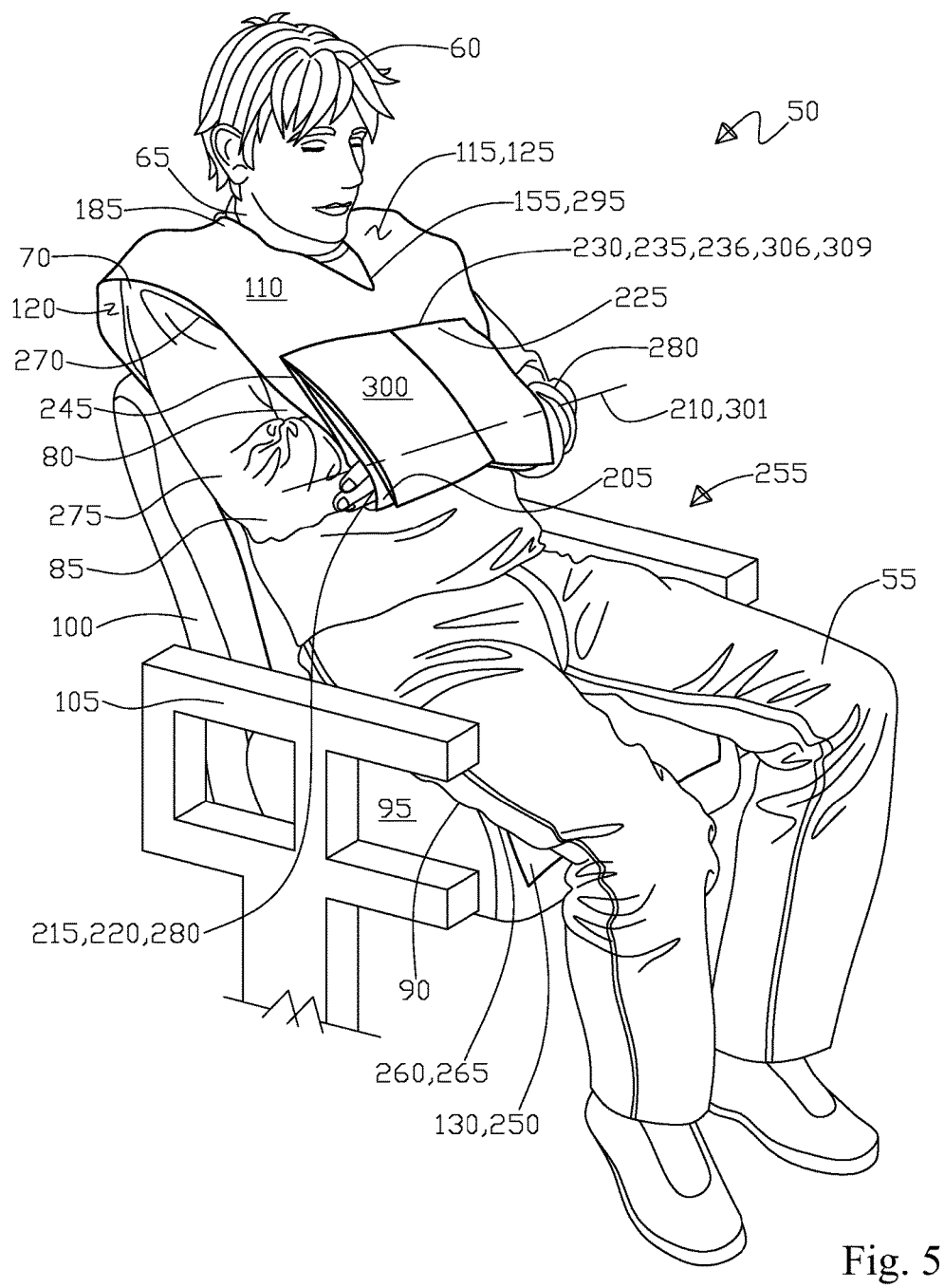
FIG. 5 shows a perspective view of the arm support apparatus in its typical use configuration in relation to the seat, showing the human, the head, the neck, the shoulders, the back, the chest, the arms, the hands, the buttocks, the seat, the seat back, the seat arms, the flexible planar member, the exterior surface, the interior surface, the front end portion, the rear end portion, the first side portion, the second side portion, the slot shaped aperture, the resting of the aperture as against the shoulders, the surrounding sidewall, the lengthwise axis, the inside surface of the sidewall, interior of the sidewall, outside surface of the sidewall, portion of the outside surface, affixing of the portion, the sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed each within a different the interior of a different sidewall, where the rear end portion is disposed on the seat and human buttocks, and the aperture not contacting the human neck from the human arm weight.

Following onward, FIG. 5 shows a perspective view of the arm support apparatus 50 in its typical use configuration in relation to the seat 95, showing the human 55, the head 60, the neck 65, the shoulders 70, the back 75, the chest 80, the arms 85, the hands 86, the buttocks 90, the seat 95, being identified as an ottoman to emphasize that the arm support apparatus 50 with only a seat 95, not requiring a seat back 100, or seat arms 105. However, FIG. 5 does show what is typically an airline, bus, or train seat 95 that usually has a back 100, and arms 105. FIG. 5 also shows the flexible planar member 110, the exterior surface 115, the interior surface 120, the front end portion 125, the rear end portion 130, the first side portion 140, the second side portion 145, the slot shaped aperture 155, the resting 185 of the aperture 155 as against the shoulders 70, the surrounding sidewall 205, the lengthwise axis 210, the inside surface 215 of the sidewall 205, interior 220 of the sidewall 205, outside surface 225 of the sidewall 205, portion 230 of the outside surface 225.

FIG. 5 additionally showing the affixing 235 of the portion 230, the sidewall 205 positioned adjacent 245 to the human chest 80, the draping 250 of the rear end portion 130 over the human back 75 and continuing past the buttocks 90, the human 55 sitting 255 upon the ottoman 95 and sitting 255 upon the rear end portion 130. FIG. 5 also shows the rear end portion 130 disposed 260 as between the ottoman 95 and the buttocks 90, the frictional interference 265 of the rear end portion 130 disposed 260 as between the ottoman 95 and the human buttocks 90, the interior surface 120 of the front end portion 125 being adjacent 270 to the human chest 80. Further, FIG. 5 shows the positioning 275 the human arms 85 to be adjacent to the exterior surface 115 on the front end portion 125, the portion 280 of the human arms 85 that are each manually disposed within the different interior 220 of the different sidewall 205, where the rear end portion 130 is disposed 260 on the seat 95 and human buttocks 90, and the aperture 155 not contacting the human neck 65 from the human arm weight 285 as the weight 285 is supported solely by the frictional interference 265.

Figure 6:
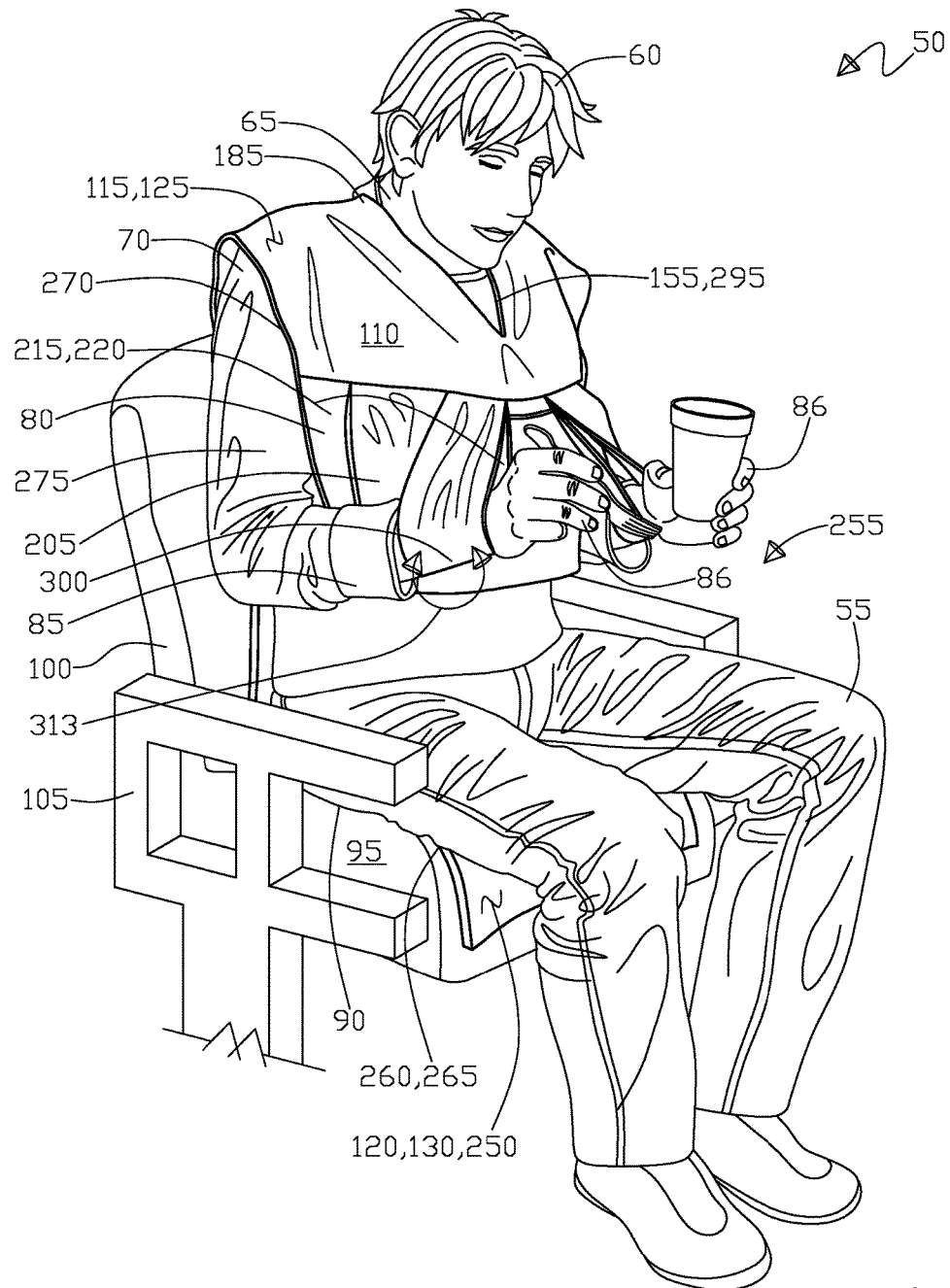
FIG. 6 shows a perspective view of the arm support apparatus in an alternative use configuration in relation to the seat, showing the human leaning forward, wherein the human back is not in contact with the seat back, as can be the case when the human is utilizing their hands for eating, drinking, working on laptop computers, working on tablet computers, playing game consoles, and the like, utilizing the alternative configuration of the surrounding sidewall, also the human head, the neck, the shoulders, the back, the chest, the arms, the hands, the buttocks, the seat, the seat back, the seat arms, the flexible planar member, the exterior surface, the interior surface, the front end portion, the rear end portion, the first side portion, the second side portion, the slot shaped aperture, the resting of the aperture as against the shoulders, the surrounding sidewall, the inside surface of the sidewall, interior of the sidewall, outside surface of the sidewall, portion of the outside surface, affixing of the portion, the sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed within the interior of the sidewall, where the rear end portion is disposed on the seat and human buttocks, and the aperture not contacting the human neck from the human arm weight that is solely supported by the frictional interference of the rear end portion disposed as between the ottoman and the human buttocks.

Yet further, FIG. 6 shows a perspective view of the arm support apparatus 50 in an alternative use configuration in relation to the seat 95, showing the human 55 leaning forward, wherein the human back 75 is not in contact with the seat back 100, as can be the case when the human 55 is utilizing 300 their hands 86 for eating, drinking, working on laptop computers, working on tablet computers, playing game consoles, and the like, utilizing the alternative configuration of the surrounding sidewall 205. Also FIG. 6 shows the human head 60, the neck 65, the shoulders 70, the back 75, the chest 80, the arms 85, the hands 86, the buttocks 90, the seat 95, the seat back 100, the seat arms 105, the flexible planar member 110, the exterior surface 115, the interior surface 120, the front end portion 125, the rear end portion 130, the first side portion 140, the second side portion 145, and the slot shaped aperture 155.

FIG. 6 further shows the resting 185 of the aperture 155 as against the shoulders 70, the surrounding sidewall 205, the inside surface 215 of the sidewall 205, interior 220 of the sidewall 205, outside surface 225 of the sidewall 205, portion 230 of the outside surface 225, affixing 235 of the portion 230, with the sidewall 205 positioned 245 adjacent to the human chest 80, also the draping 250 of the rear end portion 130 over the human back 75 and continuing past the buttocks 90. FIG. 6 also shows the human 55 sitting upon the ottoman 95 and sitting upon the rear end portion 130, the rear end portion 130 disposed 260 as between the ottoman 95 and the buttocks 90, the frictional interference 265 of the rear end portion 130 disposed as between the ottoman 95 and the human buttocks 90, also the interior surface 120 of the front end portion 125 being adjacent to the human chest 80. Further, FIG. 6 shows positioning 275 of the human arms 85 to be adjacent to the exterior surface 115 on the front end portion 125, portion 280 of the human arms 85 that are manually disposed within the interior 220 of the sidewall 205, where the rear end portion 130 is disposed 260 on the seat 95 and human buttocks 90, and the aperture 155 not contacting the human neck 65 from the human arm 85 weight 285 that is solely supported by the frictional interference 265 of the rear end portion 130 disposed 260 as between the ottoman 95 and the human buttocks 90.

Figure 7:
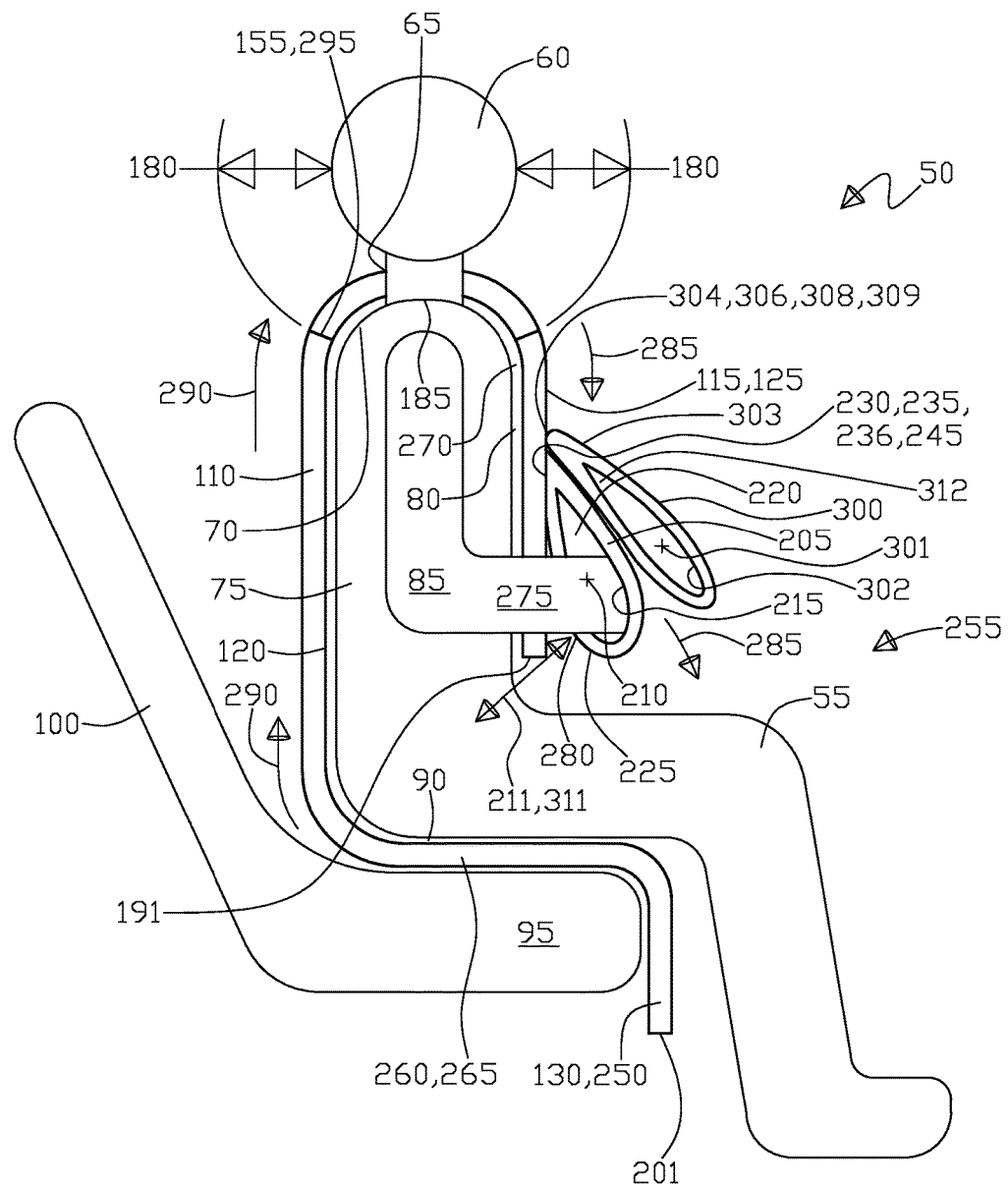
FIG. 7 shows a simplified side elevation view for pictorial clarity of the arm support apparatus in an alternative use configuration in relation to the seat, showing the human leaning forward (or sitting upward with a reclined seat back as shown), wherein the human back is not in contact with the seat back, also shown is the human head, the neck, the shoulders, the back, the chest, the arms, the hands, the buttocks, the seat, the seat back, the flexible planar member, the exterior surface, the interior surface, the front end portion, the rear end portion, the slot shaped aperture, the resting of the aperture as against the shoulders, the surrounding sidewall, the inside surface of the sidewall, interior of the sidewall, outside surface of the sidewall, portion of the outside surface, affixing of the portion, the sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed within the interior of the sidewall, where the rear end portion is disposed on the seat and human buttocks, and the aperture not contacting the human neck from the human arm weight turning into a downward force that translates into an upward force that is solely supported by the frictional interference of the rear end portion disposed as between the ottoman and the human buttocks.

Continuing, FIG. 7 shows a simplified side elevation view for pictorial clarity of the arm support apparatus 50 in an alternative use configuration in relation to the seat 95, showing the human 55 leaning forward (or sitting upward with a reclined seat back as shown), wherein the human back 75 is not in contact with the seat back 100, also shown is the human head 60, the neck 65, the shoulders 70, the back 75, the chest 80, the arms 85, the hands 86, the buttocks 90. FIG. 7 also shows the flexible planar member 110, the exterior surface 115, the interior surface 120, the front end portion 125, the rear end portion 130, the slot shaped aperture 155, the resting 185 of the aperture 155 as against the shoulders 70, the surrounding sidewall 205, the inside surface 215 of the sidewall 205, interior 220 of the sidewall 205, outside surface 225 of the sidewall 205, portion 230 of the outside surface 225, and the affixing 235 of the portion 230. FIG. 7 also shows the clearance for freely passing 180 of the aperture 155 over the human head 60 with the end result of the aperture 155 not having contact 295 upon the human neck 65 from force 285.

Wherein FIG. 7 shows the sidewall 205 positioned 245 adjacent to the human chest 80, the draping 250 of the rear end portion 130 over the human back 75 and continuing past the buttocks 90, the human 55 sitting upon the ottoman 95 and sitting upon the rear end portion 130, the rear end portion 130 disposed 260 as between the ottoman 95 and the buttocks 90, the frictional interference 265 of the rear end portion 130 disposed as between the ottoman 95 and the human buttocks 90. Further FIG. 7 shows the interior surface 120 of the front end portion 125 being adjacent to the human chest 80, positioning 275 the human arms 85 to be adjacent to the exterior surface 115 on the front end portion 125, portion 280 of the human arms 85 that are manually disposed within the interior 220 of the sidewall 205. With FIG. 7 displaying where the rear end portion 130 is disposed 260 on the seat 95 and human buttocks 90, and the aperture 155 not contacting 295 the human neck 65 from the human arm 85 weight 285 turning into a downward force 285 that translates into an upward force 290 that is solely supported by the frictional interference 265 of the rear end portion 130 disposed as between the ottoman 95 and the human buttocks 90.

Figure 8:
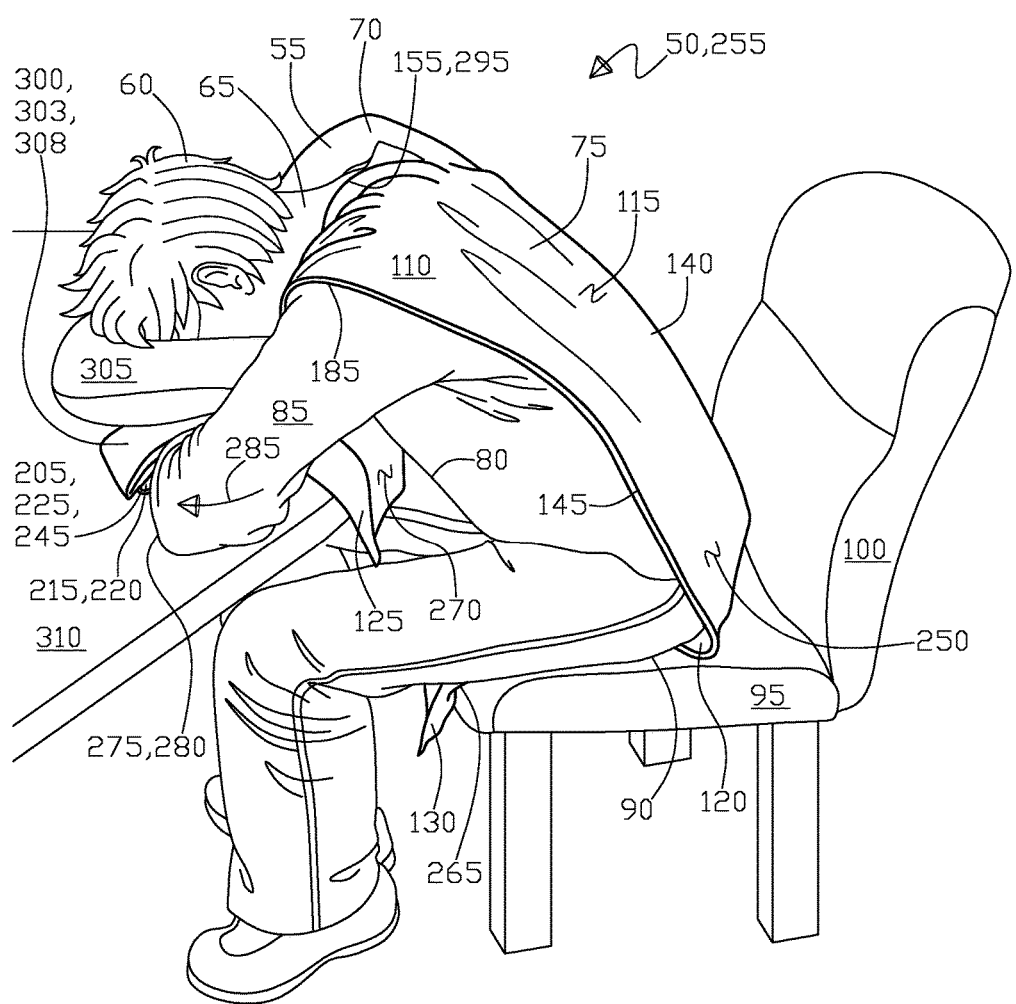
FIG. 8 shows a perspective view of the arm support apparatus in another alternative use configuration in relation to the seat, showing the human leaning far forward, wherein the human back is not in contact with the seat back, as can be the case when the human is utilizing their arms and hands for utilizing a desk or tray table for placing their head upon further using a "U" shaped pillow to sleep on, with the arms being retained by the interior of the surrounding sidewall to keep the pillow in place laterally on the desk or tray table, also shown is the human neck, the shoulders, the back, the chest, the arms, the buttocks, the seat, the seat back, the flexible planar member, the exterior surface, the interior surface, the front end portion, the rear end portion, the first side portion, the second side portion, the slot shaped aperture, the resting of the aperture as against the shoulders, the surrounding sidewall, the inside surface of the sidewall, interior of the sidewall, outside surface of the sidewall, sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed within the interior of the sidewall, where the rear end portion is disposed on the seat and human buttocks, and the aperture not contacting the human neck from the human arms pushing away from the human chest via the human head exerting downward force upon the desk or tray table, wherein the human arms pushing away from the human chest that is solely resisted by the frictional interference of the rear end portion disposed as between the ottoman and the human buttocks.

Next, FIG. 8 shows a perspective view of the arm support apparatus 50 in another alternative use configuration in relation to the seat 95, showing the human 55 leaning far forward, wherein the human back 75 is not in contact with the seat back 100, as can be the case when the human 55 is utilizing their arms 85 and hands 86 for a desk or tray table 310 to place their head 60 upon further using a "U" shaped pillow 305 to sleep on, with the arms 85 being retained by the interior 220 of the surrounding sidewall 205 to keep the pillow 305 in place laterally on the desk or tray table 310. FIG. 8 also shows the human neck 65, the shoulders 70, the back 75, the chest 80, the arms 85, the buttocks 90, the seat 95, the seat back 100, the flexible planar member 110, the exterior surface 115, the interior surface 120, the front end portion 125, the rear end portion 130, the first side portion 140, the second side portion 145, the slot shaped aperture 155, the resting 185 of the aperture 155 as against the shoulders 70.

In addition FIG. 8 shows the surrounding sidewall 205, the inside surface 215 of the sidewall 205, interior 220 of the sidewall 205, outside surface 225 of the sidewall 205, the sidewall 205 positioned 245 adjacent to the human chest 80, also the draping 250 of the rear end portion 130 over the human back 75 and continuing past the buttocks 90. Further, FIG. 8 shows the human 55 sitting upon the ottoman 95 and sitting upon the rear end portion 130, the rear end portion 130 disposed 260 as between the ottoman 95 and the buttocks 90, with the frictional interference 265 of the rear end portion 130 disposed 260 as between the ottoman 95 and the human buttocks 90.

FIG. 8 also shows the interior surface 120 of the front end portion 125 being adjacent to the human chest 80, positioning 275 the human arms 85 to be adjacent to the exterior surface 115 on the front end portion 125, portion 280 of the human arms 85 that are manually disposed within the interior 220 of the sidewall 205. Further, FIG. 8 shows where the rear end portion 130 is disposed 260 on the seat 95 and human buttocks 90, and the aperture 155 not contacting 295 the human neck 65 from the human arms 85 pushing away 285 from the human chest 80 via the human head 60 exerting downward force upon the desk or tray table 310, wherein the human arms 85 pushing away 285 from the human chest 80 that is solely resisted by the frictional interference 265 of the rear end portion 130 disposed as between the ottoman 95 and the human buttocks 90.

Figure 9:
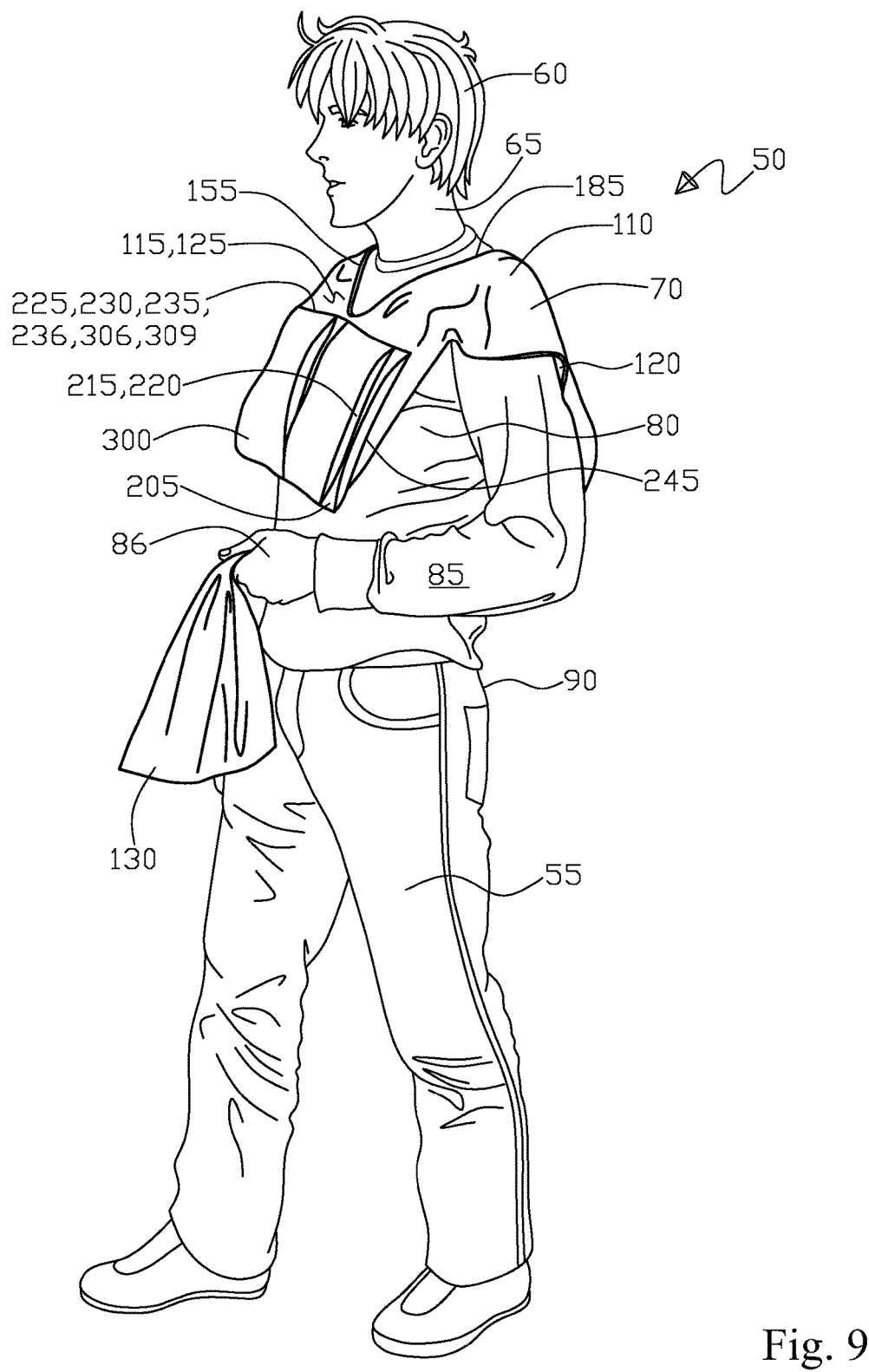
FIG. 9 shows a perspective view of the arm support apparatus wherein the human has exited from their seat with no restrictions for a restroom break with the arm support apparatus remaining in place with the aperture resting upon the human shoulders, with the rear end portion being easily pulled out of the way by the human's hand grasping the rear end portion, also shown is the human head, the human neck, the human back, the human chest, the human arms, the human hands, the human buttocks, the flexible planar member, the exterior surface, the interior surface, the front end portion, the rear end portion, the flexible surrounding sidewall, the inside surface, the outside surface, the interior, the portion of the outside surface, affixing of the portion of the outside surface to the exterior surface, and the sidewall positioned adjacent to the human chest.

Continuing, FIG. 9 shows a perspective view of the arm support apparatus 50 wherein the human 55 has exited from their seat 95 with no restrictions for a restroom break with the arm support apparatus 50 remaining in place with the aperture 155 resting 185 upon the human shoulders 70, with the rear end portion 130 being easily pulled out of the way by the human's hand 86 grasping the rear end portion 130. Also, FIG. 9 shows the human head 60, the human neck 65, the human back 75, the human chest 80, the human arms 85, the human hands 86, and the human buttocks 90. Further, FIG. 9 shows the flexible planar member 110, the exterior surface 115, the interior surface 120, the front end portion 125, the rear end portion 130, the flexible surrounding sidewall 205, the inside surface 215, the outside surface 225, the interior 220, the portion 230 of the outside surface 225, affixing 235 of the portion 230 of the outside surface 225 to the exterior surface 115, and the sidewall 205 positioned 245 adjacent to the human chest 80.

Figure 10:
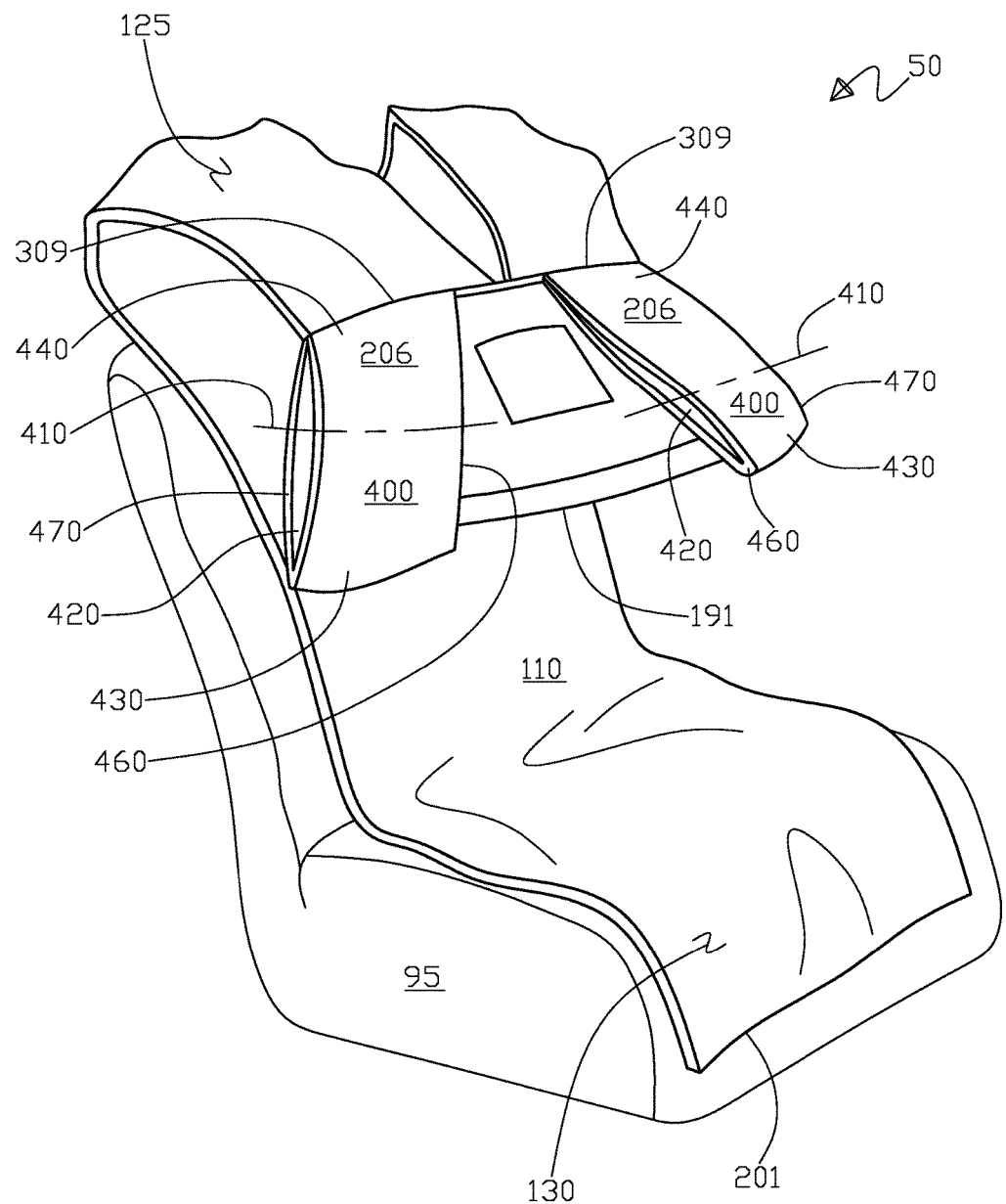
FIG. 10 shows a perspective view of the arm support apparatus in its typical use configuration in relation to the seat, except with the human removed for pictorial clarity, thus is shown the seat back, the flexible planar member, the exterior surface, the interior surface, the front end portion, the rear end portion, the first side portion, the second side portion, the slot shaped aperture, the surrounding outbound sidewall, the inside surface of the outbound sidewall, interior of the outbound sidewall, outside surface of the outbound sidewall, portion of the outside surface, affixing of the portion, and where the rear end portion is disposed on the seat and human buttocks (not shown)

Next, FIG. 10 shows a perspective view of the arm support apparatus 50 in its typical use configuration in relation to the seat 95, except with the human 55 removed for pictorial clarity, thus is shown the seat back 100, the flexible planar member 110, the exterior surface 115, the interior surface 120, the front end portion 125, the rear end portion 130, the first side portion 140, the second side portion 145, the slot shaped aperture 155. Further shown in FIG. 10 is the surrounding outbound sidewall 206, the inside surface 420 of the outbound sidewall 206, interior 450 of the outbound sidewall 206, outside surface 430 of the outbound sidewall 206, portion 440 of the outside surface 430, affixing 309 of the portion 440, and where the rear end portion 130 is disposed on the seat 95 and human buttocks 90 (not shown).

Figure 11:
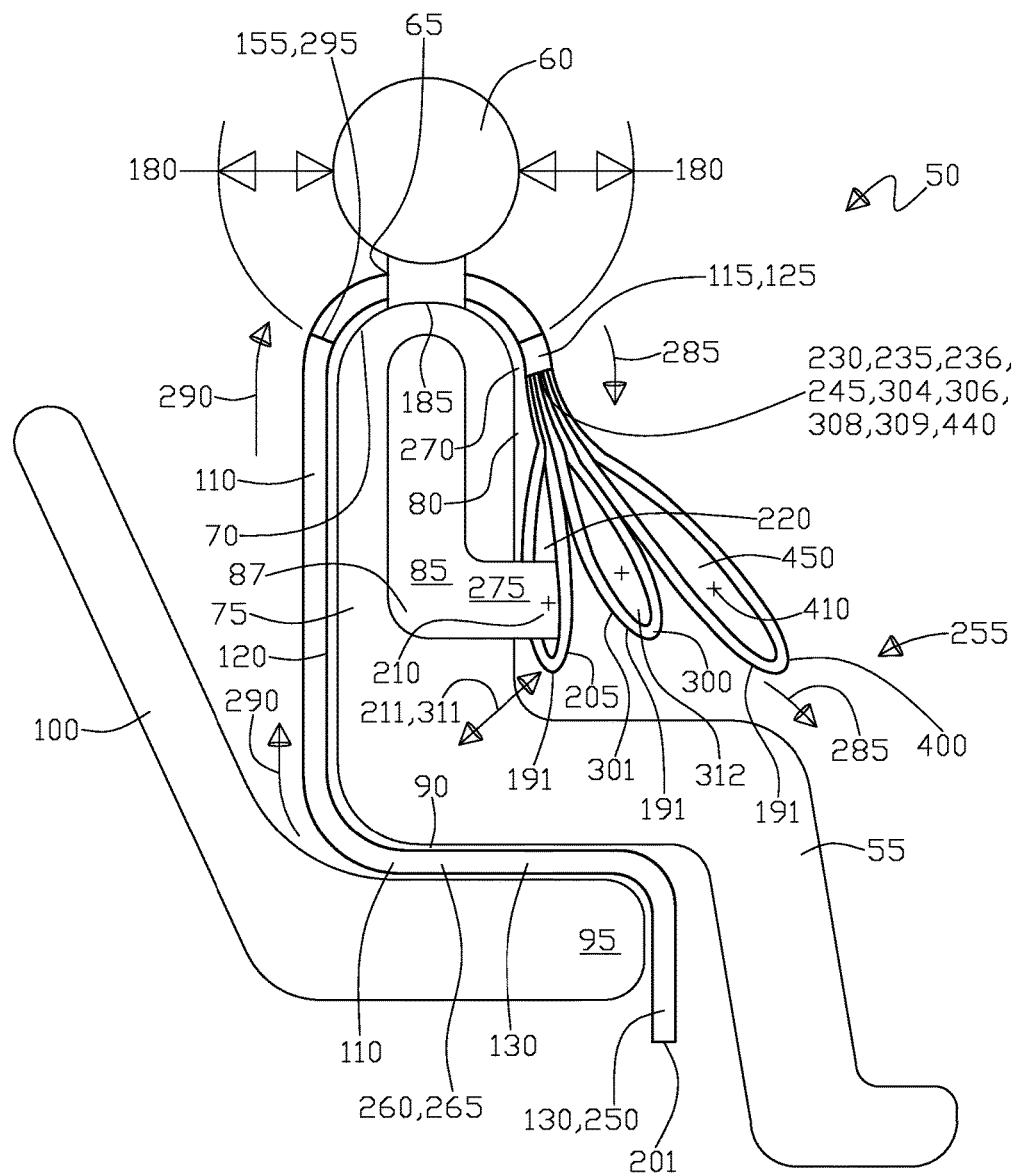
FIG. 11 shows a simplified side elevation view for pictorial clarity of the arm support apparatus similar to FIG. 7, wherein Figure shows in an alternative use configuration in relation to the seat, showing the human leaning forward (or sitting upward with a reclined seat back as shown), wherein the human back is not in contact with the seat back, also shown is the human head, the neck, the shoulders, the back, the chest, the arms, the hands, the buttocks, the seat, the seat back, the flexible planar member, the exterior surface, the interior surface, the front end portion, the rear end portion, the slot shaped aperture, the resting of the aperture as against the shoulders, the surrounding sidewall, the inside surface of the sidewall, interior of the sidewall, outside surface of the sidewall, portion of the outside surface, affixing of the portion, the sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed within the interior of the sidewall, wherein also shown are the alternate branched configuration of the surrounding sidewall, and further the outbound sidewall, also where the rear end portion is disposed on the seat and human buttocks, and the aperture not contacting the human neck from the human arm weight turning into a downward force that translates into an upward force that is solely supported by the frictional interference of the rear end portion disposed as between the ottoman and the human buttocks.

Further, FIG. 11 shows a simplified side elevation view for pictorial clarity of the arm support apparatus similar to FIG. 7, wherein Figure shows in an alternative use configuration in relation to the seat 95, showing the human 55 leaning forward (or sitting upward with a reclined seat back as shown), wherein the human back 75 is not in contact with the seat back 100, also shown is the human head 60, the neck 65, the shoulders 70, the back 75, the chest 80, the arms 85, the hands 86, the buttocks 90, the seat 95, the seat back 100, the flexible planar member 110, the exterior surface 115, the interior surface 120, the front end portion 125, the rear end portion 130, and the slot shaped aperture 155. Also FIG. 11 shows the resting of the aperture 155 against the shoulders 70, the surrounding sidewall 205, the inside surface 215 of the sidewall 205, interior 220 of the sidewall 205, outside surface 225 of the sidewall 205, portion 230 of the outside surface 225, affixing 235 of the portion 230, the sidewall 205 positioned adjacent to the human chest 80, the draping 250 of the rear end portion 130 over the human back 75 and continuing past the buttocks 90, the human 55 sitting upon the ottoman 95 and sitting upon the rear end portion 130, the rear end portion 130 disposed 260 as between the ottoman 95 and the buttocks 90.

Wherein FIG. 11 shows the frictional interference 265 of the rear end portion 130 disposed as between the ottoman 95 and the human buttocks 90, the interior surface 120 of the front end portion 125 being adjacent to the human chest 80, positioning 275 the human arms 85 to be adjacent to the exterior surface 115 on the front end portion 125, portion 280 of the human arms 85 that are manually disposed within the interior 220 of the sidewall 205. Wherein FIG. 11 also shows are the alternate branched configuration 300 of the surrounding sidewall 205, and further the outbound sidewall 400, also where the rear end portion 130 is disposed 260 on the seat 95 and human buttocks 90, and the aperture 155 not contacting 295 the human neck 65 from the human arm 85 weight 285 turning into a downward force 285 that translates into an upward force 290 that is solely supported by the frictional interference 265 of the rear end portion 130 disposed as between the ottoman 95 and the human buttocks 90.

Figure 12:
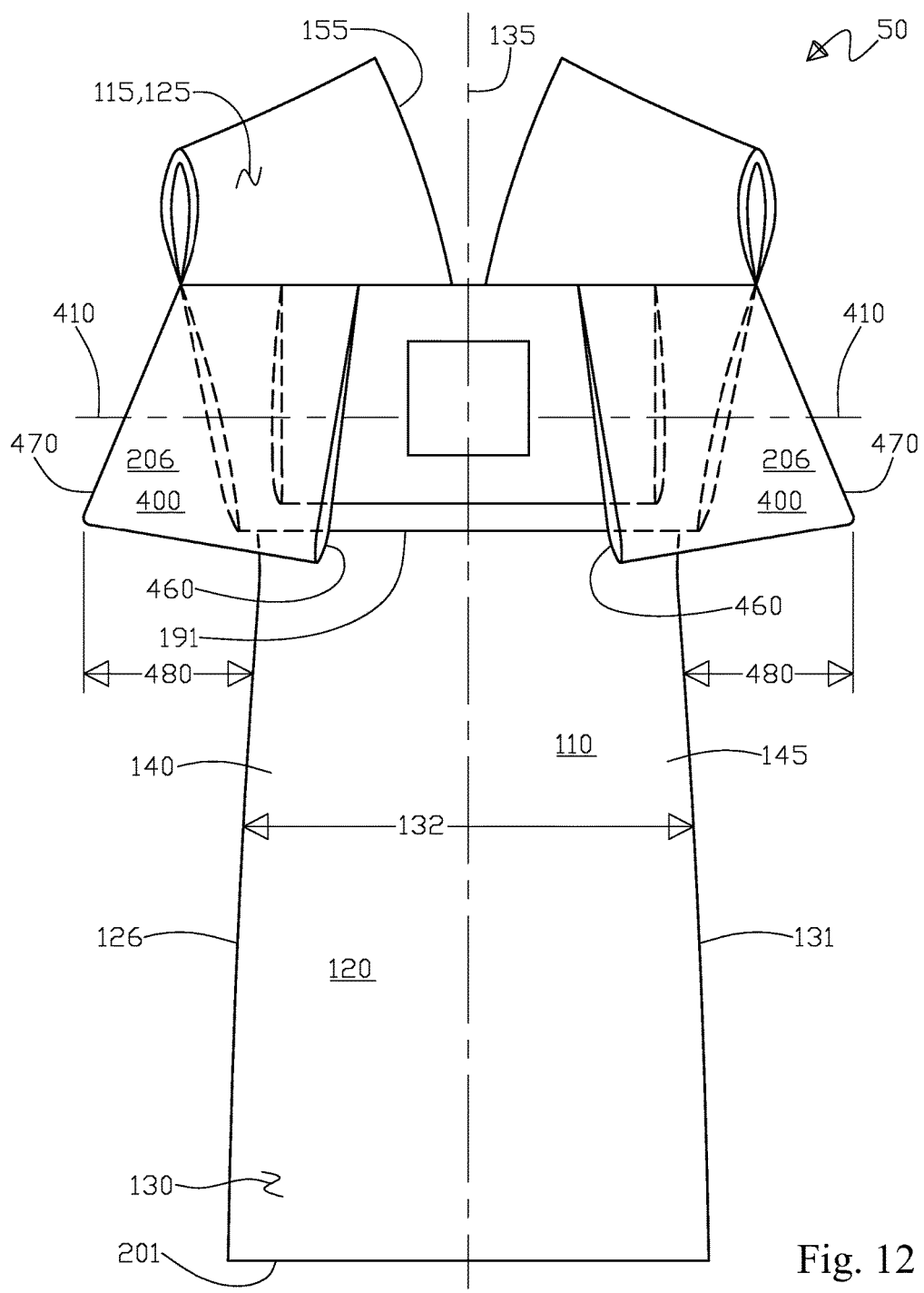
FIG. 12 shows a folded pattern view of the arm support apparatus from the exterior surface side for the front end portion and the interior surface of the rear end portion all of the flexible planar member, the longitudinal axis, the first side portion, the second side portion, the slot shaped aperture, the surrounding outbound sidewall, the lengthwise axis, outside surface of the outbound sidewall, portion of the outside outbound sidewall surface, and affixing of the outbound sidewall portion.

Moving onward, FIG. 12 shows a folded pattern view of the arm support apparatus 50 from the exterior surface 115 side for the front end portion 125 and the interior surface 120 of the rear end portion 130 all of the flexible planar member 110, the longitudinal axis 135, the first side portion 140, the second side portion 145, the slot shaped aperture 155, the surrounding outbound sidewall 206, the lengthwise axis 410, outside surface 430 of the outbound sidewall 206, portion 440 of the outside outbound sidewall surface 430, and affixing 309 of the outbound sidewall 206 portion 440.

Figure 13:
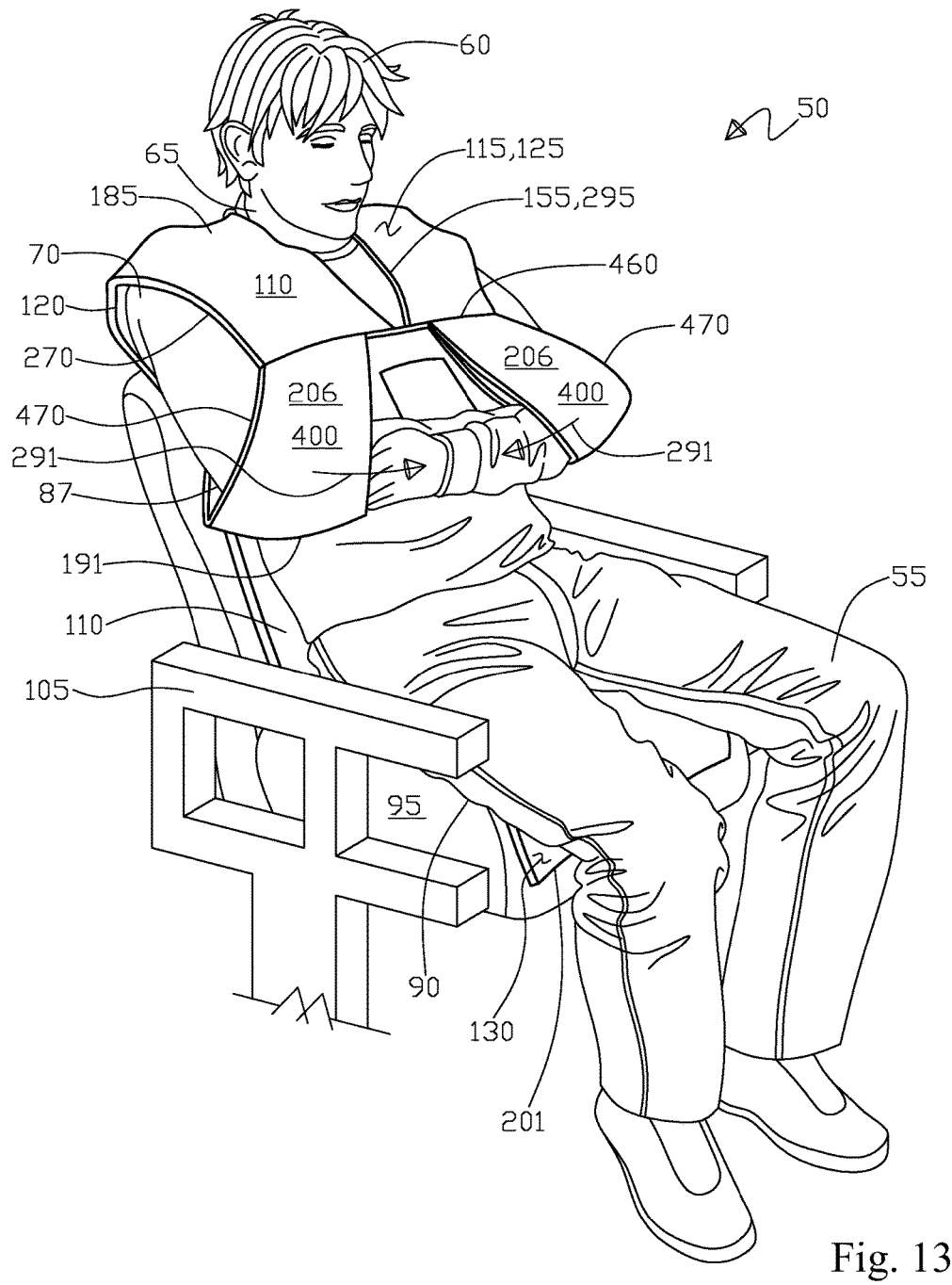
FIG. 13 shows a perspective view of the arm support apparatus in its typical use configuration in relation to the seat, showing the human, the head, the neck, the shoulders, the back, the chest, the arms, the hands, the buttocks, the seat, the seat back, the seat arms, the flexible planar member, the exterior surface, the interior surface, the front end portion, the rear end portion, the first side portion, the second side portion, the slot shaped aperture, the resting of the aperture as against the shoulders, the surrounding outbound sidewall, the inside surface of the outbound sidewall, interior of the outbound sidewall, outside surface of the outbound sidewall, portion of the outbound sidewall outside surface, affixing of the outbound sidewall portion, the outbound sidewall positioned adjacent to the human chest, the draping of the rear end portion over the human back and continuing past the buttocks, the human sitting upon the ottoman and sitting upon the rear end portion, the rear end portion disposed as between the ottoman and the buttocks, the frictional interference of the rear end portion disposed as between the ottoman and the human buttocks, the interior surface of the front end portion being adjacent to the human chest, positioning the human arms to be adjacent to the exterior surface on the front end portion, portion of the human arms that are manually disposed within the interior of the outbound sidewall, where the rear end portion is disposed on the seat and human buttocks, and the aperture not contacting the human neck from the human arm weight.

Further, FIG. 13 shows a perspective view of the arm support apparatus 50 in its typical use configuration in relation to the seat 95, showing the human 55, the head 60, the neck 65, the shoulders 70, the back 75, the chest 80, the arms 85, the hands 86, the buttocks 90, the seat 95, the seat back 100, the seat arms 105, the flexible planar member 110, the exterior surface 115, the interior surface 120, the front end portion 125, the rear end portion 130, the first side portion 140, the second side portion 145, the slot shaped aperture 155, the resting 185 of the aperture 155 as against the shoulders 70, the surrounding outbound sidewall 206. In addition, FIG. 13 shows the lengthwise axis 135, the inside surface 420 of the outbound sidewall 206, interior 450 of the outbound sidewall 206, outside surface 430 of the outbound sidewall 206, portion 440 of the outbound sidewall 206 outside surface 430, affixing 309 of the outbound sidewall 206 portion 440, the outbound sidewall 206 positioned adjacent to the human chest 80, the draping 250 of the rear end portion 130 over the human back 75 and continuing past the buttocks 90.

Also, FIG. 13 shows the human 55 sitting 255 upon the ottoman 95 and sitting 255 upon the rear end portion 130, the rear end portion 130 disposed as between the ottoman 95 and the buttocks 90, the frictional interference 265 of the rear end portion 130 disposed as between the ottoman 95 and the human buttocks 90, the interior surface 120 of the front end portion 125 being adjacent to the human chest 80, positioning the human arms 85 to be adjacent to the exterior surface 115 on the front end portion 125, portion of the human arms 85 that are manually disposed within the interior 450 of the outbound sidewall 206, where the rear end portion 130 is disposed on the seat 95 and human buttocks 90, and the aperture 155 not contacting the human neck 65 from the human arm weight 285.

Figure 14:
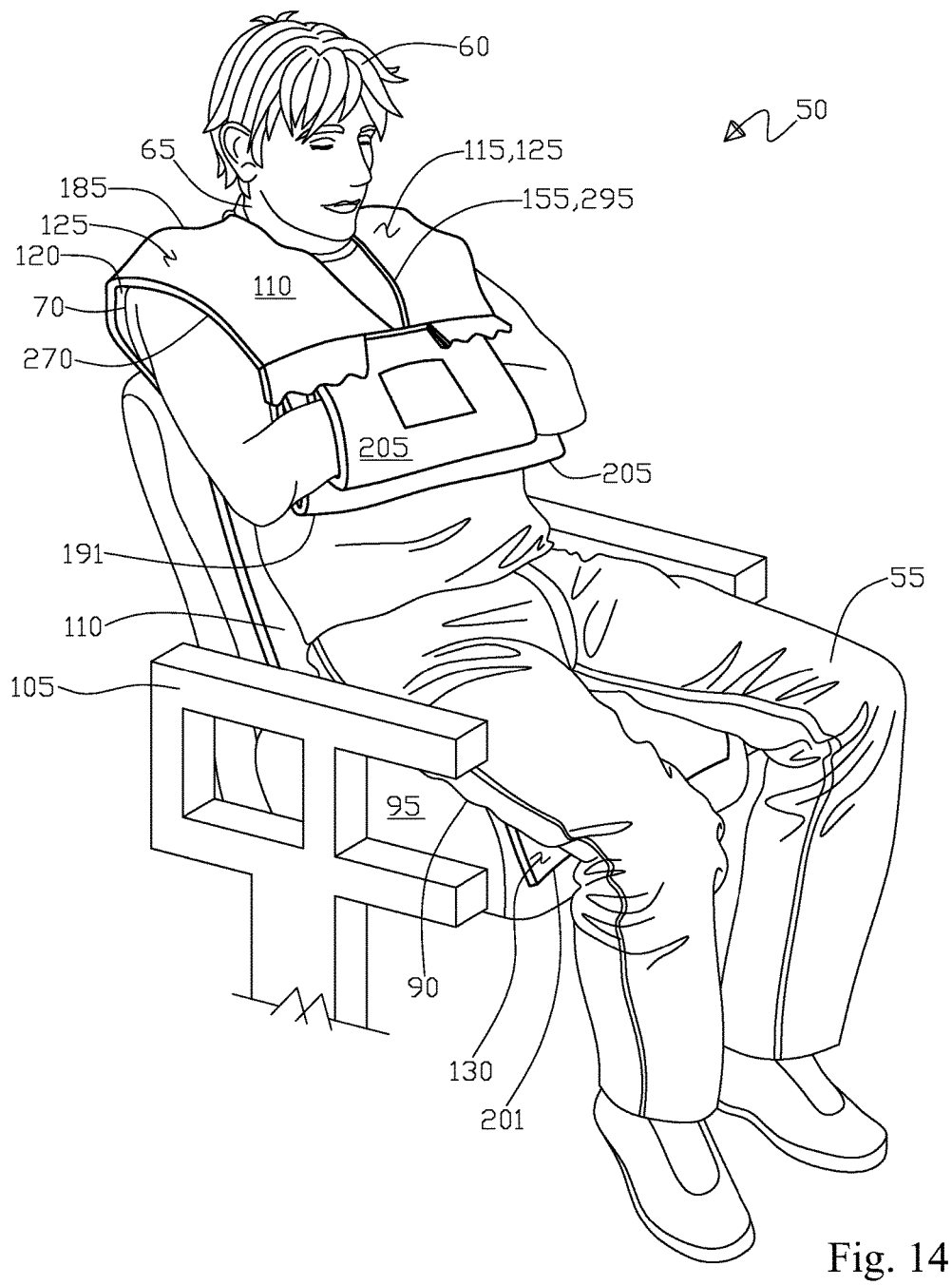
FIG. 14 is similar to FIG. 5 except for both arms are disposed within the single sidewall furthest from the chest as opposed to FIG. 5 that shows the arms each inserted into different branched sidewalls.
Figure 15:
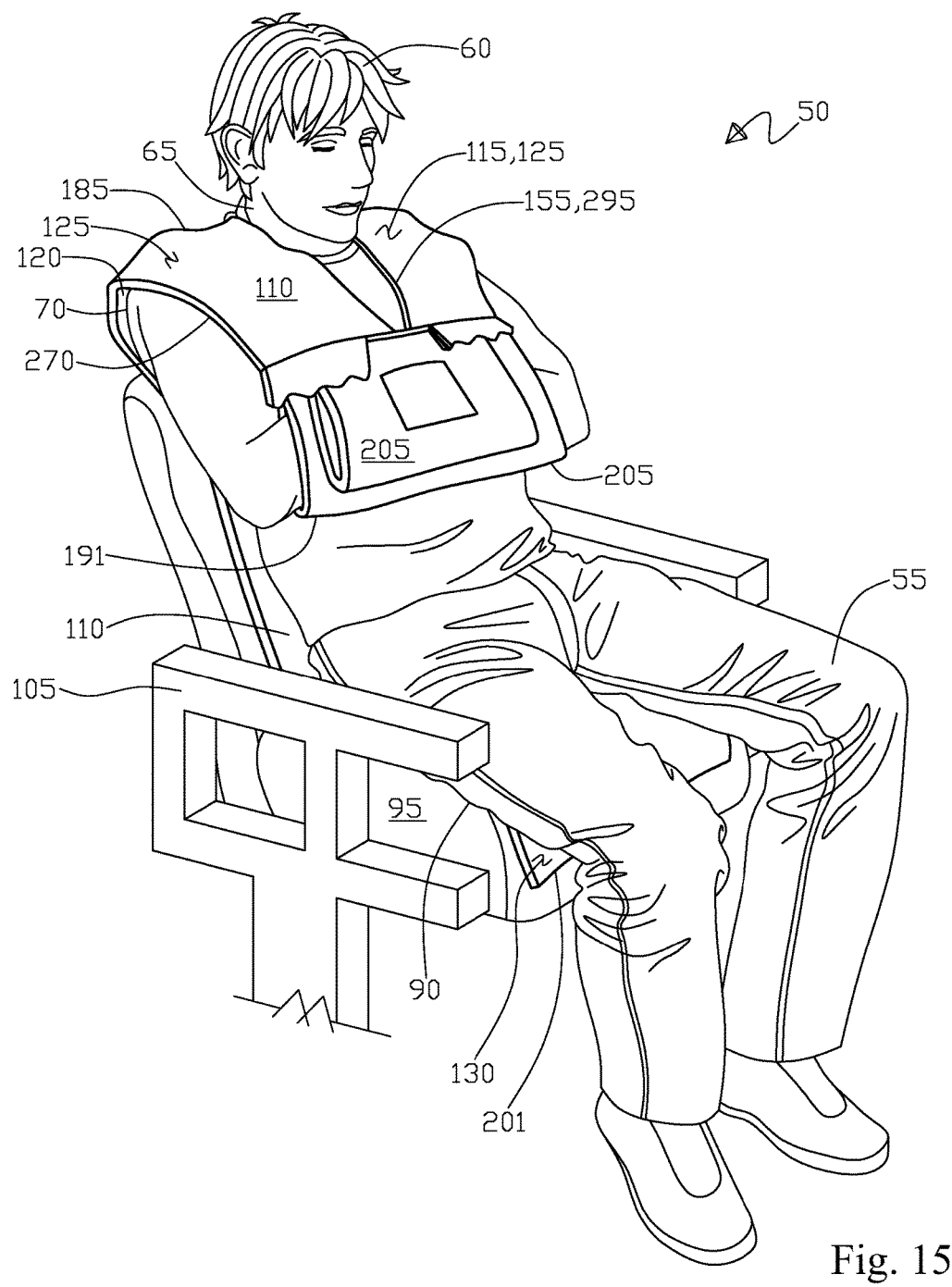
FIG. 15 is similar to FIG. 14 except for both arms are disposed within the single sidewall closest to the chest, however, noting that each arm could be disposed within each one of the sidewalls one being closest to the chest and one being furthest from the chest.

Continuing, FIG. 14 is similar to FIG. 5 except for both arms 85 are disposed within the single sidewall 205 furthest from the chest 80 as opposed to FIG. 5 that shows the arms 85 each inserted into different branched sidewalls 300. Next, FIG. 15 is similar to FIG. 14 except for both arms 85 are disposed within the single sidewall 205 closest to the chest 80, however, noting that each arm 85 could be disposed within each one of the sidewalls 205 one being closest to the chest 80 and one being furthest from the chest 80.

Broadly, the human arm support apparatus 50 is for use with a human 55 seated only upon an ottoman 95, not having a seat back 100 or seat arms 105, with the human 55 having a head 60, neck 65, shoulders 70, back 75, chest 80, arms 85, and buttocks 90, with the human arm support apparatus 50 including the flexible planar member 110 having an exterior surface 115 and an opposing interior surface 120, see FIGS. 1 to 3, and FIGS. 5 to 9. The flexible planar member 110 also having the front end portion 125 and opposing rear end portion 130 with the longitudinal axis 135 spanning therebetween. The flexible planar member 110 also having the first side portion 140 and the opposing second side portion 145 with the transverse axis 150 spanning therebetween, see FIG. 2 for the best detail. Further included is the slot shaped aperture 155 is positioned therethrough the flexible planar member 110 from the exterior surface 115 to the interior surface 120.

The slot 155 positioning is dictated by having its longer major axis 160 coincident 170 with the longitudinal axis 135 and the slot 155 has a shorter minor axis 165 coincident with the transverse axis 150, see FIG. 2 for the flat pattern layout of the flexible planar member 110 giving the detail of the aperture 155 configuration. Also, the aperture 155 is sized and configured to be larger than the human head 60 to freely pass 180 over the human head 60 to rest against the human's shoulders 70, see in particular FIG. 7 that shows the large size of the aperture 155 in relation to the human head 60, with the goal being too easily and freely 180 put on and take off the flexible planar member 110 via putting the human's head 60 through the larger aperture 155, this also accommodates not disturbing large hairdos, hats, and the like.

Looking at FIG. 2 in particular, the aperture 155 has a width 156 parallel to the transverse 150 and minor 165 axes, the aperture 155 width 156 is at least one-half of the side distance 132, further the aperture 155 has an aperture length 157 parallel to the longitudinal 135 and major 160 axes that is at least equal to a front portion distance 190 defined as between the front margin 191 and the transverse 150 and minor 165 axes.

Further, in use the aperture 155 is not to come into contact 295 with the human neck 65 to enhance the human's comfort level, as the downward force 285 from the arms 85 is supported by the frictional interference 265 as between the human buttocks 90 and the seat 95 with the rear end portion 130 disposed therebetween, see FIG. 7 in particular and FIGS. 1, 5, and 6, also. In addition, the transverse axis 150 is positioned to be asymmetrically closer 190 to the front end portion 125 and the transverse axis 150 is positioned to be asymmetrically further 200 from the rear end portion 130, as best shown in FIG. 2 being the flat pattern layout of the flexible planar member 110, this also can be seen in FIG. 1, with the rear end portion 130 being a longer extension from the aperture 155 to facilitate the frictional interference 265 as previously described, also FIG. 1 shows the front end portion 125 having a much shorter extension from the aperture 155 to only accommodate attached the surrounding sidewall for supporting the human arms 85. The preferred materials of construction for the flexible planar member 110 are bed-sheet type material; however, other similar materials would be acceptable.

Looking in particular at FIGS. 1, 2, 3, 5, 6, 7, 8, 10 to 15, wherein the rear end portion 130 defined as a rear end portion distance 200 along the longitudinal axis 135 as between the rear margin 201 and the transverse axis 150 that is at least two times longer than the front end portion 25 defined as a front portion distance 190 along the longitudinal axis 135 as between the front margin 191 and the transverse axis 150 to operationally help ensure that the rear end portion 130 is disposed between the human buttocks 90 and the ottoman 95 see in particular FIG. 2 and FIGS. 1, 10, plus 7, 11, 5, 6, and 13 to 15.

Further included in the human arm support apparatus 50 is the flexible surrounding sidewall 205 that is about the lengthwise axis 210, with the sidewall 205 having an inside surface 215 that defines a sidewall interior 220 and the sidewall 205 also having the outside surface 225, wherein a portion 230 of the outside surface 225 is affixed 235 to the exterior surface 115 on the front end portion 125 being positioned such that the lengthwise axis 210 is parallel 240 to the transverse axis 150, see in particular FIG. 2, also see FIGS. 1 and 3. The sidewall 205 is preferably constructed of the same material as the flexible planar member 110 and the affixing 235 is preferably by sewing, however, other methods of affixing are acceptable, or even making the flexible planar member 110 and the sidewall 205 integral to one another. Note that there may be more than one sidewall 205, wherein each human arm 85 could be disposed in each one of a multiple of sidewalls 205, wherein each sidewall 205 could be positioned at different heights for comfort. Also pockets can be added to the front end portion 125 as desired out of the same material as the flexible planar member 110.

Operationally and in use, the aperture 155 is freely passed 180 over the human head 60 with the interior surface 120 resting 185 against the human shoulders 70, see FIGS. 5, 6, and 7, in particular. Further, the sidewall 205 is being positioned adjacent 245 to the human chest 80 and the rear end portion 130 is draped 250 over the human back 75 and continuing beyond the human buttocks 90, the human 55 then sits upon the ottoman 95 essentially sitting on a part 260 of the rear end portion 130 thus the part 260 is disposed 260 as between the ottoman 95 and the human buttocks 90, thus creating the frictional interference 265, see FIGS. 1, 5, 6, 7 and 8.

Further, the front end portion 125 interior surface 120 is adjacent to the human chest 80, wherein the human arms 85 are then positioned 275 adjacent to the exterior surface 115 of the front end portion 125 wherein a portion 280 of the human arms 85 are manually disposed within the interior 220 to act as a hanging support for the arms 85, see FIGS. 1, 5, 6, and 7. Wherein the arms 85 weight results in a downward force 285 on the front end portion 125 that translates to an upward force 290 on the rear end portion 130 that is completely supported by the frictional interference 265 as between the rear end portion 130 part 260 that is disposed 260 between the human buttocks 90 and the ottoman 95 resulting in no necessary or needed contact 295 of the aperture 155 upon the human neck 65 from the downward force 285 to maximize comfort for the human 55, see FIG. 7 in particular.

Further, in looking at FIGS. 1 to 3, 5, 7, and 9, of the human arm support apparatus 50, the portion of the outside surface 225 being affixed to the exterior surface 115 is constructed of a single straight transverse line attachment 236. Wherein the single straight transverse line attachment 236 is parallel to the transverse axis 150, the single straight transverse line attachment 236 structurally results in the surrounding sidewall 205 formed into a single attachment loop, as best shown in FIG. 7, that has pivotal movement 211 to increase freedom of movement of the lengthwise axis 210 and the surrounding sidewall 205 to increase human arm 85 comfort.

Continuing, in looking at FIGS. 2 and 7, for the human arm support apparatus 50, the rear end portion 130 is at least two times longer than the front end portion 125 along the longitudinal axis 135 to help ensure that the rear end portion 130 is disposed 260 between the human buttocks 90 and the ottoman 95. Also, on the human arm support apparatus 50, the flexible planar member 110 and the flexible surrounding sidewall 205 are preferably constructed of fabric and the single straight transverse line attachment 236 is preferably constructed of stitching.

As an alternative, as shown in FIGS. 1 to 3 and 5 to 9, a pair of separately branched flexible surrounding sidewalls 300 that are both about a branched sidewall axis 301 are shown, with the branched sidewalls 300 each having a branched sidewall inside surface 302 that defines a branched sidewall interior 312 and each branched sidewall 300 also has an branched sidewall outside surface 303. Further, a portion 304 of the branched outside surface 303 is affixed 306 to the exterior surface 115 on the front end portion 125 being positioned 307 such that the branched sidewall 300 axis 301 is parallel to the transverse axis 150. Operationally, in use the aperture 155 is freely passed over the human head 60 with the interior surface 120 resting against the human shoulders 70, the pair of branched sidewalls 300 are positioned separately adjacent 308 to the human chest 80 and the rear end portion 130 is draped 250 over the human back 75 and continuing beyond the human buttocks 90, the human 55 then sits upon the ottoman 95 essentially sitting on a part of the rear end portion 130 thus the rear end portion 130 is disposed 260 as between the ottoman 95 and the human buttocks 90, see FIGS. 1, 5, 6, and 7 in particular. As the front end portion 125 interior surface 120 is adjacent to the human chest 80, the human arms 85 are then positioned adjacent to the exterior surface 115 of the front end portion 125, wherein each of the human arms 85 are manually disposed within each one of the pair of branched sidewall 300 interiors 312 are to act as independent supports for each of the arms 85. Wherein the arms 85 weight results in a downward force 285 on the front end portion 125 that translates to an upward force 290 on the rear end portion 130 that is completely supported by a frictional interference 265 as between the rear end portion 130 disposed 260 between the human buttocks 90 and the ottoman 95, resulting in no contact 295 of the aperture 155 upon the human neck 65 from the downward force 285, see in particular FIG. 7.

Continuing, in looking at FIGS. 1 to 3, 5 to 7, and 9, for the human arm support apparatus 50, the portion of the branched outside surface 303 being affixed to the exterior surface 115, is preferably constructed of a split single straight transverse line attachment 309, wherein the split single straight transverse line attachment 309 is parallel to the transverse axis 150. The split single straight transverse line attachment 309 structurally results in each branched surrounding sidewall 300 formed into a single attachment loop that has pivotal movement 311 to increase freedom of movement of the branched sidewall axis 301 and the branched surrounding sidewall 300 including a rotational movement 313 at and from the branched sidewall 300 and the split attachment 309 to increase human arm 85 mobility comfort to facilitate the arm 85 to be able to consume food, drink, work on laptop computers, work on tablet computers, play game consoles, and the like, see in particular FIG. 6.

Also on the human arm support apparatus 50 the flexible planar member 110 and the pair of separately branched flexible surrounding sidewalls 300, 400 are preferably constructed of fabric, further, the split single straight transverse line attachment 309 is preferably constructed of stitching.

As a second alternative, in looking at FIGS. 10, 11, 12, and 13 a pair of separately branched outbound 400 flexible surrounding sidewalls 206 that are both about a branched outbound sidewall axis 410, the branched outbound sidewalls 206 each having a branched outbound sidewall 206 inside surface 420 that defines a branched outbound sidewall 206 interior 450 and each branched outbound sidewall 206 also has an branched outbound sidewall 206 outside surface 430. Further, each branched outbound surrounding sidewall 206 also has an inner edge margin 460 and an opposing outer edge margin 470 with the branched outbound sidewall 206 axis 410 spanning therebetween, a portion of the branched outbound sidewall 206 outside surface 430 is affixed 309 to the exterior surface 115 on the front end portion 125 being positioned such that the branched outbound sidewall 206 axis 410 is parallel to the transverse axis 150.

Continuing, looking at particular at FIGS. 12 and 13, the pair of outbound sidewalls 206 are further positioned such that the outer edge margin 470 extends for an extension distance 480 beyond the first side margin 126 and the second side margin 131 respectively, each extension distance 480 is at least one-half a distance 132 as between the first side margin 126 and the second side margin 131, wherein operationally in use see FIG. 13, the aperture 155 is freely passed over the human head with the interior surface 120 resting against the human shoulders 70, the pair 400 of branched outbound sidewalls 206 are positioned separately adjacent to the human chest 80 and the rear end portion 130 is draped 250 over the human back 75 and continuing beyond the human buttocks 90, the human 55 then sits upon the ottoman 95 essentially sitting on a part of the rear end portion 130. Thus the rear end portion 130 is disposed as between the ottoman 95 and the human buttocks 90, as the front end portion 125 interior surface 120 is adjacent to the human chest 80, the human arms 85 are then positioned adjacent to the exterior surface 115 of the front end portion 125, wherein each of the human arms 85 are manually disposed within each one of the pair of branched outbound 400 sidewall 206 interiors 450 to act as independent supports for each of the arms 85 with the outbound sidewall 206 outer edge margin 470 supporting the arm 85 going past an elbow 87 toward the shoulder 70, wherein the arms 85 weight results in an inward force 291 on the arms 85 from the outbound 400 sidewalls 206 outer edge margins 470 to keep the arms 85 from extending outwardly beyond the chair 95 arms 105 see in particular FIG. 13. Further, the arms 85 weight results in a downward force 285 on the front end portion 125 that translates to the upward force 290 on the rear end portion 130 that is completely supported by a frictional interference 265 as between the rear end portion 130 disposed 260 between the human buttocks 90 and the ottoman 95 resulting in no contact 295 of the aperture 155 upon the human neck 65 from the downward force 285, see FIGS. 11 and 13.

CONCLUSION

Accordingly, the present invention of the arm support apparatus has been described with some degree of particularity directed to the embodiments of the present invention. It should be appreciated, though; that the present invention is defined by the following claims construed in light of the prior art so modifications or changes may be made to the exemplary embodiments of the present invention without departing from the inventive concepts contained therein.

The invention claimed is:

1. A human arm support apparatus for use with a human seated only upon an ottoman, the human having a head, neck, shoulders, back, chest, arms, and buttocks, said human arm support apparatus comprising:

(a) a flexible planar member having an exterior surface and an opposing interior surface, said flexible planar member also having a front end portion terminating in a front margin and an opposing rear end portion terminating in a rear margin with a longitudinal axis spanning therebetween, said flexible planar member also having a first side portion terminating in a first side margin and an opposing second side portion terminating in a second side margin defining a side distance as between said first and second side margins with a transverse axis spanning therebetween, a slot shaped aperture therethrough said flexible planar member from said exterior surface to said interior surface, said slot has a longer major axis coincident with said longitudinal axis and said slot has a shorter minor axis coincident with said transverse axis, said aperture has a width parallel to said transverse and minor axes, said aperture width is at least one-half of said side distance, further said aperture has an aperture length parallel to said longitudinal and major axes that is at least equal to a front portion distance defined as between said front margin and said transverse and minor axes, said aperture is sized and configured to be larger than the human head to freely pass over the human head to rest against the shoulders, said transverse axis is positioned to be asymmetrically closer to said front end portion and said transverse axis is positioned to be asymmetrically further from said rear end portion, wherein said rear end portion defined as a rear end portion distance along said longitudinal axis as between said rear margin and said transverse and minor axes that is at least two times longer than said front end portion defined as said front portion distance along said longitudinal axis as between said front margin and said transverse and minor axes to operationally help ensure that said rear end portion is disposed between the human buttocks and the ottoman; and (b) a flexible surrounding sidewall that is about a lengthwise axis, said sidewall having an inside surface that defines a sidewall interior and said sidewall also has an outside surface, a portion of said outside sidewall surface is affixed to said exterior surface on said front end portion being positioned such that said lengthwise axis is parallel to said transverse axis, operationally in use said aperture is configured to be freely passed over the human head with said interior surface resting against the human shoulders, said sidewall is positioned adjacent to the human chest and said rear end is draped over the human back and continuing beyond the human buttocks, the human then sits upon the ottoman essentially sitting on a part of said rear end portion thus said rear end portion is configured to position as between the ottoman and the human buttocks when the wearer is sitting on the ottoman, wherein said interior surface of said front end portion is adjacent to the human chest, the human arms are then positioned adjacent to said exterior surface of said front end portion wherein a portion of the human arms are configured to manually disposed within said interior to act as a support for the arms, wherein the arms weight results in a downward force on said front end portion that translates to an upward force on said rear end portion that is completely supported by a frictional interference as between said rear end portion disposed between the human buttocks and the ottoman resulting in no contact of said aperture upon the human neck from said downward force;

wherein said portion of said outside surface being affixed to said exterior surface is constructed of a single straight transverse line attachment, wherein said single straight transverse line attachment is parallel to said transverse axis, said single straight transverse line attachment structurally results in said surrounding sidewall formed into a single attachment loop that has pivotal movement to increase freedom of movement of said lengthwise axis and said surrounding sidewall to increase human arm comfort; wherein said single straight transverse line attachment is constructed of stitching.

2. A human arm support apparatus according to claim 1 wherein said flexible planar member and said flexible surrounding sidewall are constructed of fabric.

3. A human arm support apparatus for use with a human seated only upon an ottoman, the human having a head, neck, shoulders, back, chest, arms, and buttocks, said human arm support apparatus comprising:

(a) a flexible planar member having an exterior surface and an opposing interior surface, said flexible planar member also having a front end portion terminating in a front margin and an opposing rear end portion terminating in a rear margin with a longitudinal axis spanning therebetween, said flexible planar member also having a first side portion terminating in a first side margin and an opposing second side portion terminating in a second side margin defining a side distance as between said first and second side margins with a transverse axis spanning therebetween, a slot shaped aperture therethrough said flexible planar member from said exterior surface to said interior surface, said slot has a longer major axis coincident with said longitudinal axis and said slot has a shorter minor axis coincident with said transverse axis, said aperture has a width parallel to said transverse and minor axes, said aperture width is at least one-half of said side distance, further said aperture has an aperture length parallel to said longitudinal and major axes that is at least equal to a front portion distance defined as between said front margin and said transverse and minor axes, said transverse axis is positioned to be asymmetrically closer to said front end portion and said transverse axis is positioned to be asymmetrically further from said rear end portion, wherein said rear end portion defined as a rear end portion distance along said longitudinal axis as between said rear margin and said transverse and minor axes that is at least two times longer than said front end portion defined as said front portion distance along said longitudinal axis as between said front margin and said transverse and minor axes to operationally help ensure that said rear end portion is disposed between the human buttocks and the ottoman; and (b) a pair of separately branched flexible surrounding sidewalls that are both about a branched sidewall axis, said branched sidewalls each having a branched sidewall inside surface that defines a branched sidewall interior and each said branched sidewall also has an branched sidewall outside surface, a portion of said branched sidewall outside surface is affixed to said exterior surface on said front end portion being positioned such that said branched sidewall axis is parallel to said transverse axis, operationally in use said aperture is configured to be freely passed over the human head with said interior surface resting against the human shoulders, said pair of branched sidewalls are positioned separately adjacent to the human chest and said rear end portion is draped over the human back and continuing beyond the human buttocks, the human then sits upon the ottoman essentially sitting on a part of said rear end portion thus said rear end portion is configured to position as between the ottoman and the human buttocks when the wearer is sitting on the ottoman, wherein said interior surface of said front end portion is adjacent to the human chest, the human arms are then positioned adjacent to said exterior surface of said front end portion, wherein each of the human arms are configured manually disposed within each one of said pair of branched sidewall interiors to act as independent supports for each of the arms, wherein the arms weight results in a downward force on said front end portion that translates to an upward force on said rear end portion that is completely supported by a frictional interference as between said rear end portion disposed between the human buttocks and the ottoman resulting in no contact of said aperture upon the human neck from said downward force;

wherein said portion of said branched outside surface being affixed to said exterior surface is constructed of a split single straight transverse line attachment, wherein said split single straight transverse line attachment is parallel to said transverse axis, said split single straight transverse line attachment structurally results in each said branched surrounding sidewall formed into a single attachment loop that has pivotal movement to increase freedom of movement of said branched sidewall axis and said branched surrounding sidewall including a rotational movement at and from said branched sidewall and said split attachment to increase human arm comfort; wherein said split single straight transverse line attachment is constructed of stitching.

4. A human arm support apparatus according to claim 3 wherein said flexible planar member and said pair of separately branched flexible surrounding sidewalls are constructed of fabric.

5. A human arm support apparatus for use with a human seated only upon an ottoman, the human having a head, neck, shoulders, back, chest, arms, and buttocks, said human arm support apparatus comprising:

(a) a flexible planar member having an exterior surface and an opposing interior surface, said flexible planar member also having a front end portion terminating in a front margin and an opposing rear end portion terminating in a rear margin with a longitudinal axis spanning therebetween, said flexible planar member also having a first side portion terminating in a first side margin and an opposing second side portion terminating in a second side margin defining a side distance as between said first and second side margins with a transverse axis spanning therebetween, a slot shaped aperture therethrough said flexible planar member from said exterior surface to said interior surface, said slot has a longer major axis coincident with said longitudinal axis and said slot has a shorter minor axis coincident with said transverse axis, said aperture has a width parallel to said transverse and minor axes, said aperture width is at least one-half of said side distance, further said aperture has an aperture length parallel to said longitudinal and major axes that is at least equal to a front portion distance defined as between said front margin and said transverse and minor axes, said transverse axis is positioned to be asymmetrically closer to said front end portion and said transverse axis is positioned to be asymmetrically further from said rear end portion, wherein said rear end portion defined as a rear end portion distance along said longitudinal axis as between said rear margin and said transverse and minor axes that is at least two times longer than said front end portion defined as said front portion distance along said longitudinal axis as between said front margin and said transverse and minor axes to operationally help ensure that said rear end portion is disposed between the human buttocks and the ottoman; and (b) a pair of separately branched outbound flexible surrounding sidewalls that are both about a branched outbound sidewall axis, said branched outbound sidewalls each having a branched outbound sidewall inside surface that defines a branched outbound sidewall interior and each said branched outbound sidewall also has an branched outbound sidewall outside surface, each said branched outbound surrounding sidewall also has an inner edge margin and an opposing outer edge margin with said branched outbound sidewall axis spanning therebetween, a portion of said branched outbound sidewall outside surface is affixed to said exterior surface on said front end portion being positioned such that said branched outbound sidewall axis is parallel to said transverse axis, said pair of outbound sidewalls are further positioned such that said outer edge margin extends for an extension distance beyond said first side margin and said second side margin respectively, each said extension distance is at least one-half a distance as between said first side margin and said second side margin, wherein operationally in use said aperture is configured to be freely passed over the human head with said interior surface resting against the human shoulders, said pair of branched outbound sidewalls are positioned separately adjacent to the human chest and said rear end portion is draped over the human back and continuing beyond the human buttocks, the human then sits upon the ottoman essentially sitting on a part of said rear end portion, thus said rear end portion is configured to position as between the ottoman and the human buttocks when the wearer is sitting on the ottoman, as said front end portion interior surface is adjacent to the human chest, the human arms are then positioned adjacent to said exterior surface of said front end portion, wherein each of the human arms are configured manually disposed within each one of said pair of branched outbound sidewall interiors to act as independent supports for each of the arms with said outbound sidewall outer edge margin supporting the arm going past an elbow toward the shoulder, wherein the arms weight results in an inward force on the arms from said outbound sidewalls outer edge margins to keep the arms from extending outwardly beyond the chair arms, further the arms weight results in a downward force on said front end portion that translates to an upward force on said rear end portion that is completely supported by a frictional interference as between said rear end portion disposed between the human buttocks and the ottoman resulting in no contact of said aperture upon the human neck from said downward force;

wherein said portion of said branched outbound sidewall outside surface being affixed to said exterior surface is constructed of a split single straight transverse line attachment, wherein said split single straight transverse line attachment is parallel to said transverse axis, said split single straight transverse line attachment structurally results in each said branched surrounding outbound sidewall formed into a single attachment loop that has pivotal movement to increase freedom of movement of said branched outbound sidewall axis and said branched surrounding outbound sidewall including a rotational movement at and from said branched outbound sidewall and said split attachment to increase human arm comfort; wherein said split single straight transverse line attachment is constructed of stitching.

6. A human arm support apparatus according to claim 5 wherein said flexible planar member and said pair of separately branched flexible surrounding outbound sidewalls are constructed of fabric.

* * * * *